United States Patent [19]

Floyd, Jr. et al.

[11] 4,236,027
[45] Nov. 25, 1980

[54] NOVEL 11-ALKOXY-9-KETO (OR HYDROXY)-PROSTENOIC ACID DERIVATIVES AND METHOD FOR PREPARING SAME

[75] Inventors: Middleton B. Floyd, Jr., Suffern, N.Y.; Martin J. Weiss, Oradell, N.J.

[73] Assignee: American Cyanamid Company, Stamford, Conn.

[21] Appl. No.: 843,020

[22] Filed: Oct. 17, 1977

Related U.S. Application Data

[60] Continuation-in-part of Ser. No. 751,302, Dec. 16, 1976, abandoned, which is a continuation of Ser. No. 540,352, Jan. 10, 1975, abandoned, which is a division of Ser. No. 359,391, May 11, 1973, Pat. No. 3,876,690.

[51] Int. Cl.$^3$ ............................................. C07C 177/00
[52] U.S. Cl. ................................. 562/500; 260/408; 260/110.7 R; 260/413; 500/503; 500/118; 500/121; 502/463; 502/503
[58] Field of Search ...................... 500/118, 53, 121; 260/470.9 R, 413, 408; 362/463, 500, 503

*Primary Examiner*—Robert Gerste
*Attorney, Agent, or Firm*—Richard J. Hammond

[57] ABSTRACT

This disclosure describes certain 11-alkoxy-9-keto- (or hydroxy)-prostenoic acid derivatives useful as antimicrobial agents, hypotensive agents, anti-ulcer agents, or as intermediates.

14 Claims, No Drawings

NOVEL 11-ALKOXY-9-KETO (OR HYDROXY)-PROSTENOIC ACID DERIVATIVES AND METHOD FOR PREPARING SAME

CROSS REFERENCE TO RELATED APPLICATIONS

This application is a continuation-in-part of our copending application Ser. No. 751,302, filed Dec. 16, 1976, which is in turn a continuation of our application Ser. No. 540,352, filed Jan. 10, 1975, both now abandoned, which is in turn a divisional of our application Ser. No. 359,391, filed May 11, 1973, now U.S. Pat. No. 3,876,690.

BRIEF SUMMARY OF THE INVENTION

This invention relates to novel 11-alkoxy substituted prostanoic acids and derivatives as well as to intermediates and methods for their preparation. The novel compounds of this invention may be represented by the following general formula:

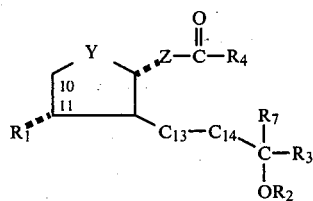

wherein $R_1$ is lower alkoxy, $\omega$-hydroxy-substituted lower alkoxy, or $\omega$-tetrahydropyranyloxy-substituted lower alkoxy; $R_2$ is hydrogen, lower alkyl, or triphenylmethyl; $R_3$ is a straight chain alkyl group having from 2 to 10 carbon atoms, a straight chain alkyl group having from 2 to 10 carbon atoms and substituted with one or two lower alkyl groups, a straight chain alkenyl methyl group having from 3 to 10 carbon atoms, a straight chain alkenyl methyl group having from 3 to 10 carbon atoms and substituted with one or two lower alkyl groups, a cycloalkyl group having from 4 to 9 carbon atoms, lower alkyl substituted cycloalkyl group having from 5 to 10 carbon atoms, a cycloalkyl-substituted lower alkyl group having from 6 to 12 carbon atoms and in which the cycloalkyl group is optionally substituted with a lower alkyl group, a cycloalkenyl group having from 5 to 9 carbon atoms, a lower alkyl substituted cycloalkenyl group having 6 to 10 carbon atoms, a cycloalkenyl substituted lower alkyl group having from 6 to 12 carbon atoms and in which the cycloalkenyl group is optionally substituted with a lower alkyl group, adamantyl, or an adamantyl substituted lower alkyl group; $R_4$ is hydroxy, an alkoxy group having from 1 to 12 carbon atoms, or tetrahydropyranyloxy; $R_7$ is hydrogen or a lower alkyl group having up to 3 carbon atoms; Y is a divalent radical selected from the group consisting of those of the formulae:

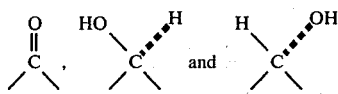

and Z is a divalent radical selected from the group consisting of those of the formulae:

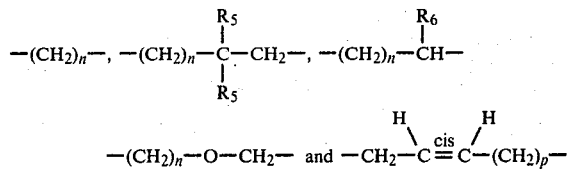

wherein n is an integer from 3 to 8, inclusive, p is an integer from 2 to 6 inclusive, $R_5$ is an alkyl group having up to 3 carbon atoms, and $R_6$ is an alkyl group having up to 3 carbon atoms, a fluorine atom or a phenyl group; and the moiety $—C_{13}-C_{14}—$ is ethylene or trans-vinylene; with the proviso that when $R_7$ is a lower aklyl group then $R_2$ is hydrogen; and all optical isomers thereof.

Also embraced within the scope of the present invention are the non-toxic, pharmaceutically acceptable salts of the novel compounds of the present invention when $R_4$ is hydroxy. The cations comprised in these salts include, for example, the non-toxic metal cations such as the sodium ion, potassium ion, calcium ion, and magnesium ion as well as the organic amine cations such as the tri(lower alkyl)- amine cations (e.g., triethylamine, triethanolamine, procaine, and the like).

The novel compounds of the present invention are obtainable as yellow oils having characteristic absorption spectra. They are relatively insoluble in water but are relatively soluble in common organic solvents such as ethanol, ethyl acetate, dimethylformamide, and the like. The cationic salts of the compounds when $R_4$ is hydroxy are, in general, white to yellow crystalline solids having characteristic melting points and absorption spectra. They are relatively soluble in water, methanol, and ethanol but are relatively insoluble in benzene, diethyl ether, and petroleum ether.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergström et al., J. Biol. Chem. 238, 3555 (1963) and Horton, Experientia 21, 113 (1965) and references cited therein. All of the so called natural prostaglandins are derivatives of prostanoic aicd:

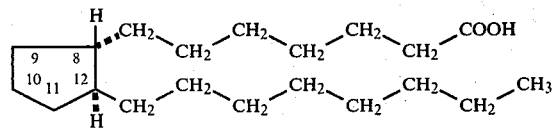

The hydrogen atoms attached to C-8 and C-12 are in trans-configuration. The natural prostaglandins represent only one of the possible optical isomers. The compounds of this convention include all possible optical isomers.

The novel compounds of the present invention may be readily prepared from certain 4-substituted cyclopentenone intermediates which may be represented by the following general formula:

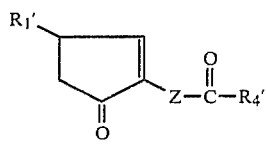

wherein $R'_1$ is lower alkoxy or ω-tetrahydropyranyloxy-substituted lower alkoxy; $R'_4$ is tetrahydropyranyloxy or an alkoxy group having from 1 to 12 carbon atoms; and Z is as hereinabove defined.

Certain of the 4-oxycyclopentenone intermediates may be prepared from the corresponding 4-unsubstituted cyclopentenones (I) in accordance with the reaction scheme of Flowsheet A, wherein Z' embraces all of Z, but not

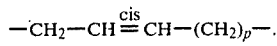

The requisite cyclopentenones are described in Belgium Pat. No. 786,215 (granted and laid open to inspection on Jan. 15, 1973) or can be obtained by analogous procedures to those described in the aforesaid patent.

In Flowsheet A which follows, Z', $R'_1$ and $R'_4$ are as hereinabove defined; R is a lower alkyl group, $R''_4$ is hydroxy or an alkoxy group having from one to 12 carbon atoms, and m is an integer from two to five inclusive.

introduction of the oxy function. This step is preferably carried out in the presence of a silver salt to facilitate the displacement of the halide ion. The particular 4-oxy derivative that is formed is determined by the nature of the solvent system. Treatment of the 4-bromocyclopentenone with silver fluoroborate in water-acetone (for solubility) provides the 4-hydroxycyclopentenone. When the solvent system is water-tetrahydrofuran, in addition to the 4-hydroxy derivative there is also obtained the 4'-hydroxybutyloxy derivative (III), formed by solvolysis with tetrahydrofuran. When the solvent is only tetrahydrofuran then only the latter compound is formed. Substitution of tetrahydrofuran with alcohols, e.g., methanol, ethanol, isopropanol, butanol and the like, provides the 4-alkoxycyclopentenones (IV). With ethylene glycol or propylene glycol etc. the corresponding 4-(ω-substituted hydroxy alkoxy)cyclopentenone (V) is obtained. In the latter three procedures it is preferably to add a proton acceptor which will not react with (II), for example, sym-collidine.

In general these procedures are operable with either the free carboxylic acid or alkyl carboxylate, as desired. A particular alkyl carboxylate not provided by formula (I) can be obtained by hydrolysis to the acid and esterification in the usual way, for example with the appropriate alcohol, or for a t-butyl ester with isobutylene. However, for the subsequent alanate conjugate addition process it is necessary to utilize a cyclopentenone wherein the carboxylic acid as well as all free hydroxyl

FLOWSHEET A

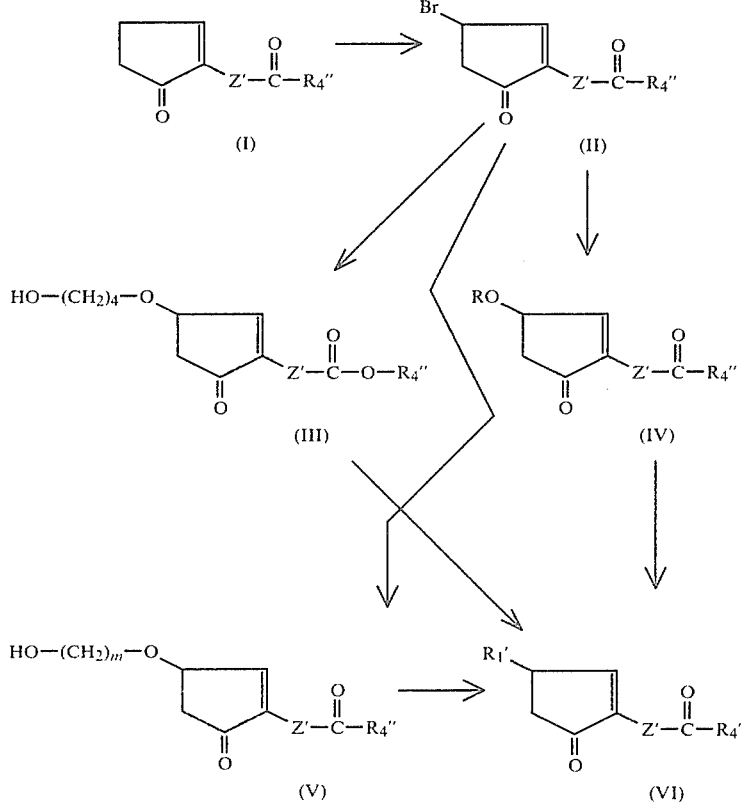

Introduction of the 4-oxy function into the 4-unsubstituted cyclopentenones (I) is accomplished by first halogenating the 4-position with an allylic halogenating reagent, preferably N-bromosuccinimide. The resulting 4-bromocyclopentenones (II) is then solvolyzed for the groups are blocked. A particularly useful blocking group for both functions is the tetrahydropyranyl group since the group can easily be cleaved with weak acid under conditions which do not disrupt the subsequently-prepared, relatively-unstable 11-oxy-9-keto system (β-oxy-ketone). Thus, it is not possible to effect a satisfactory chemical hydrolysis of an alkyl ester or of an O-alkanoyl group in an 11-oxy-9-keto prostanoic acid derivative under conditions to which this system is stable (enzymatic hydrolysis is possible). Of course these stability considerations do not apply in the "F" (9-hydroxy) series.

The 9-keto-13-trans-prostenoic acids and esters of this invention may be prepared via the novel conjugate addition process outlined in the Flowsheet B which follows. In Flowsheet B, $R_3$, $R'_1$, $R'_4$, $R''_4$, and Z are as defined hereinabove; $R_8$ is a lower alkyl group (each of the three $R_8$ radicals bonded to a aluminum does not necessarily have to be the same), $R'_2$ is lower alkyl or triphenyl methyl, $R''$ is hydrogen or lower alkyl and $R''_2$ is lower alkoxy or ω-hydroxy-substituted lower alkoxy.

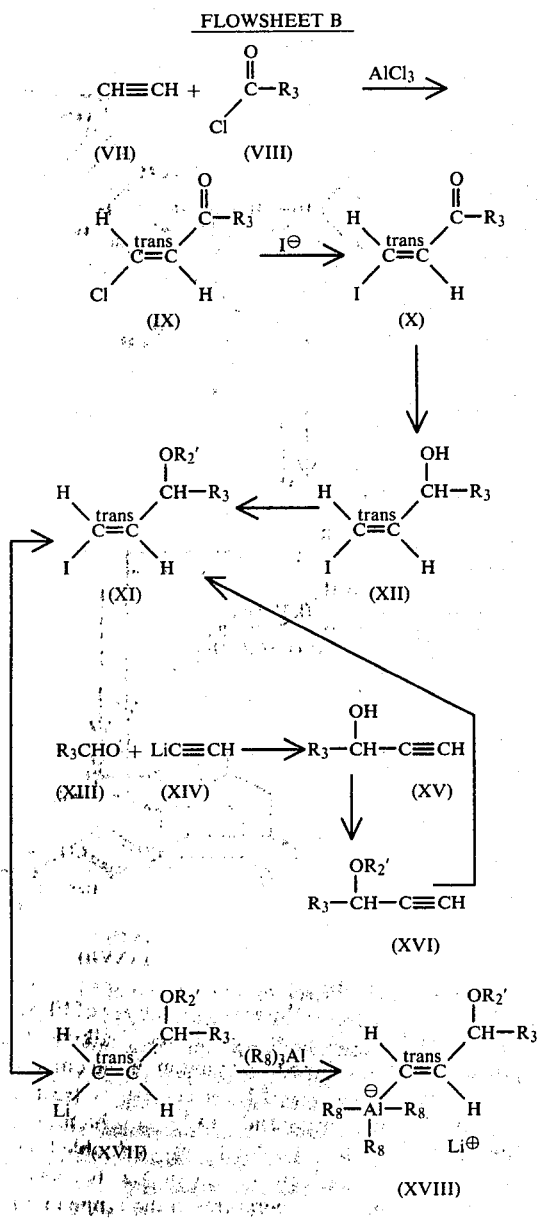

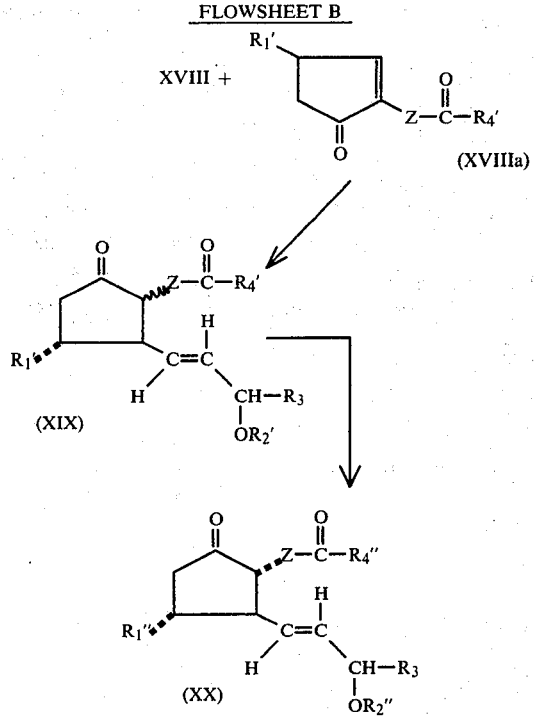

In accordance with the reaction scheme of Flowsheet B, acetylene (VII) is treated with an appropriate acid chloride (VIII) in the presence of aluminum trichloride to provide the 1-chloro-3-keto-trans-1-alkene (IX). Interchange with sodium iodide, preferably in a ketone solvent such as acetone, provides the corresponding trans-vinyl iodide (X). Reduction of the keto function in (X) with sodium borohydride furnishes the alcohol (XII), which is then blocked with the triphenylmethyl group or a triphenylmethyl group substituted with one or two methoxy groups or an O-lower alkyl group is introduced. Blocking the hydroxy function can also be accomplished with a trialkylsilyl group.

The blocked trans-vinyl iodide can also be obtained by treatment of the appropriate aldehyde (XIII) with lithium acetylide (XIV) in the usual manner, blocking the product 3-hydroxy-1-alkyne (XV) and then, in one operation, treating the resulting (XVI) successively with disiamylborane, trimethylamine N-oxide, and iodine and aqueous sodium hydroxide to give (XI). This latter procedure is preferred when $R_3$ is adamantyl, contains a center of unsaturation, a cyclopropyl ring or other relatively sensitive feature.

The blocked vinyl iodide (XI) is then submitted to metal interchange with an alkyl lithium, e.g. n-butyl lithium, at very low temperatures, e.g. −78° C., which provides the vinyl lithium derivative (XVII), the trans-configuration of the double bond being retained. After one to four hours, addition of a trialkyl aluminum [$(R_8)_3Al$], preferably trimethyl aluminum, to the solution of the lithio derivative (XVII) furnishes the lithio alanate intermediate (XVIII), also with retention of the trans-configuration of the double bond. The cycloalkenone (XVIII), dissolved in ether or other non-protoropic solvent, is then added to the alanate solution. The resulting solution is allowed to warm to room temperature and is kept for about six to eighteen hours at ambient temperatures. Potential hydroxy or carboxylic acid groups in cycloalkenone (XVIIIa) are blocked as ethers or esters, respectively, with tetrahydropyranyl and/or trialkylsilyl groups. Interchange of alanate (XVIII) with cycloalkenone (XVIIIa) results in the transfer of the trans-1-alkenyl ligand in (XVIII) with retention of the trans-configuration in a 1,4-conjugate manner to the cycloalkenone (XVIIIa) furnishing, after quenching the reaction solution, the 1,4-conjugate addition product (XIX). It is important to note too that the trans-alkenyl ligand from (XVIII) adds trans to the 4-substituent in (XVIIIa). In (XIX) we are however not certain of the relative configuration of the side chains to each other. The situation is indicated in structure (XIX) by the ~ bond between the ring and the

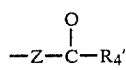

chain and is indicated in the nomenclature of the compounds involved by the designation 8 $\overline{\overline{\xi}}$. In any event deblocking to (XX) with acid, e.g. treatment with acetic acid: tetrahydrofuran:water in the ratio of 3:1:1 at 35°–45° C. for from three to forty-eight hours, results in the trans-relationship between the chains. This procedure results in de-O-tritylation as well as hydrolysis of tetrahydropyranyl and trialkylsilyl groups. Alkyl esters are not cleaved by this procedure, however these esters can be hydrolized by enzymatic or microbiological techniques known to the art.

In order to ensure a trans-relationship in (XIX) these products can be submitted to conditions known in the literature to equilibrate the 8-iso PGE$_1$ to a mixture containing about 90% of the trans product. These conditions involve treatment with potassium acetate in aqueous methanol for 96 hours at room temperature.

An alternative route, also involving conjugate addition of an alanate to a cycloalkenone, is outlined in Flowsheet C, which follows. In Flowsheet C, R$_3$, R$_8$, Z, R$'_1$, R$'_4$, and R$''_4$ are as hereinabove defined.

FLOWSHEET C

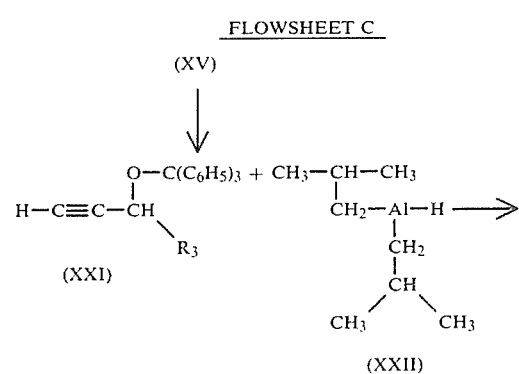

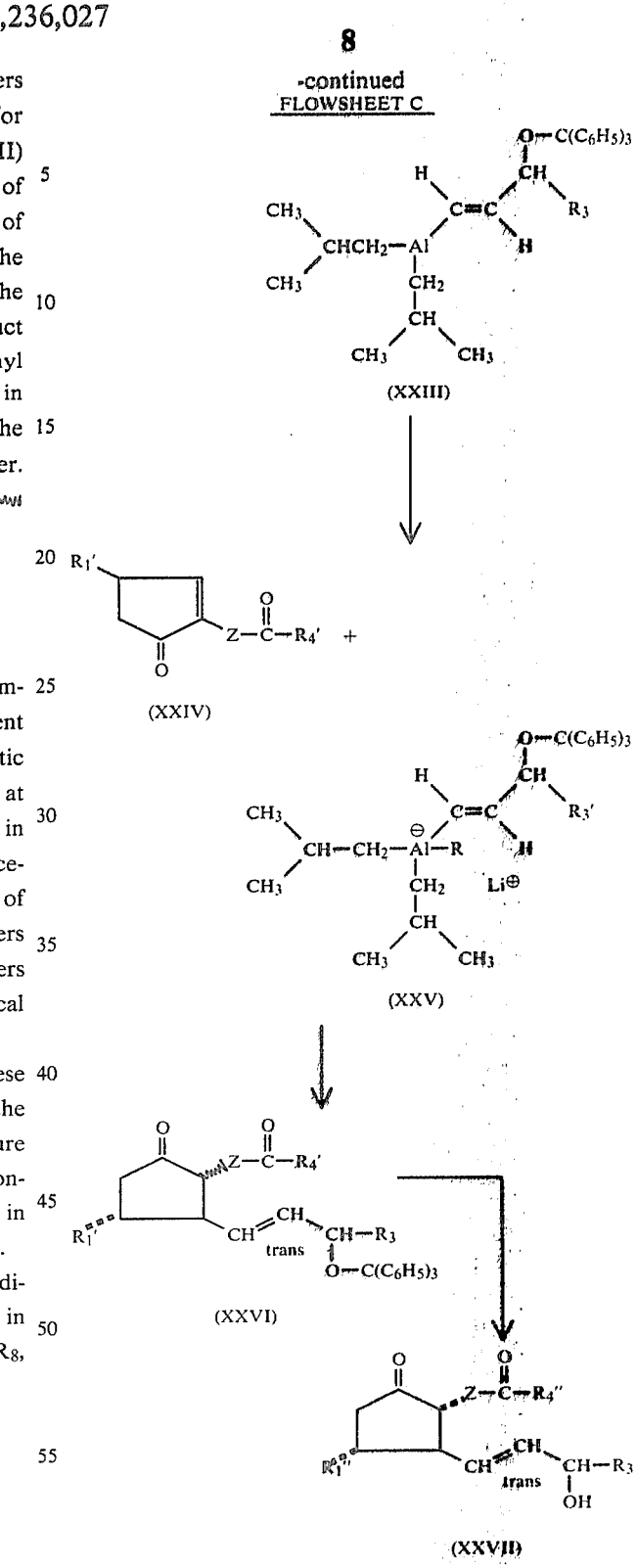

In accordance with the reaction scheme of Flowsheet C, the triphenylmethoxy substituted 1-alkyne (XXI), prepared by O-triphenylmethylation of the corresponding 1-alkyne-3-ol (XV, Flowsheet B), is treatd with diisobutylaluminum hydride (XXII), which provides the alane (XXIII) containing the trans-double bond and is carried out in an inert solvent such as benzene, toluene, and the like at temperatures in the range of 40°–60°

C. for several hours. It can also be carried out in a solvent such as tetrahydrofuran, usually in an approximate 2:1 mixture with benzene or hexane; in which case the reaction requires somewhat more vigorous conditions, usually heating at about 70° C.-75° C. for about eighteen hours. The subsequent reaction with methyl or n-butyl lithium ($R_8$-Li) is preferably carried out in a mixture of the above solvents with an ether-type solvent such as diethyl ether, dibutyl ether, tetrahydrofuran and the like. This reaction is rapid and is preferably carried out at 0° C.-10° C, with cooling. The conjugate 1,4-addition of the resulting alanate salt (XXV) to the 4-oxy-cyclopent-2-en-1-one (XXIV) is preferably carried out at ambient temperatures for a period of 12 to 24 hours. This reaction is also best carried out in an ether-type solvent such as diethyl ether, dibutyl ether, tetrahydrofuran, and the like. The intermediate alanate-enolate adduct is then carefully hydrolyzed in situ, with dilute hydrochloric acid with cooling, and the product (XXVI) is isolated in the usual manner, well known in the art. Removal of tetrahydropyranyl blocking groups and of the triphenylmethyl blocking group can then be accomplished by treating with weak acid. A preferred procedure involves heating at 45° C. for 3.5 hours in a solvent system consisting of acetic acid:tetrahydrofuran:water in the proportion of 4:2:1. If (XXVI) is a tetrahydropyranyl ester, there is then obtained the prostenoic acid (XXVII, R″$_4$=hydroxy).

The 9-keto derivatives (XXVIII) of this invention can be converted to the corresponding 9-hydroxy derivatives. If this conversion is effected with sodium borohydride, the product is a mixture of 9α- and 9β-hydroxy derivatives (XXIX) and (XXX) as set forth in the following reaction scheme:

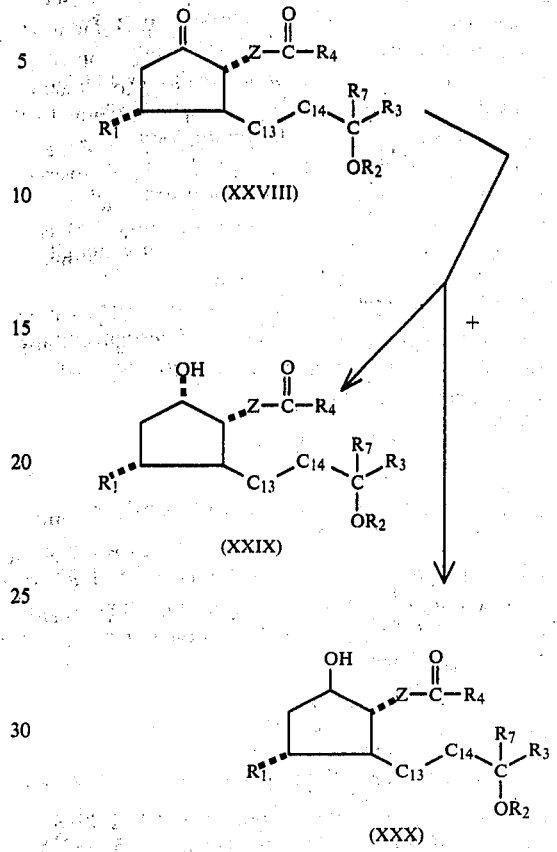

In Flowsheet D, $R_1$, $R_2$, $R_3$, $R_4$, $R_7$, Z and —$C_{13}$–$C_{14}$—are as hereinabove defined. When the reaction is carried out with lithium perhydro-9b-boraphenylyl hydride [H. C. Brown and W. C. Dickason, Journ. Amer. Chem. Soc., 92, 709 (1970)] the product is at least predominantly the 9α-hydroxy derivative (XXIX), wherein the 9-hydroxy group is cis to the side-chain attached to $C_8$ and to the 11-oxy function.

Those compounds of this invention embodying the —$CH_2$–$CH_2$—linkage at —$C_{13}$–$C_{14}$—may be prepared from the corresponding $\Delta^{13}$ derivatives, obtained via the alanate process, by catalytic reduction, preferably at low pressure with a noble metal catalyst in an inert solvent at ambient temperatures.

In accordance with accepted convention, an α-substituent at the 8-, 9-, 11- or 12-positions is behind the plane of the paper whereas a β-substituent at these positions is in front of the plane of paper. This is usually represented by a ••• bond for a α-substituent, a — bond for a β-substituent, and a ⌇ bond where both are indicated. Thus, the 9-hydroxy derivatives may be variously represented as follows:

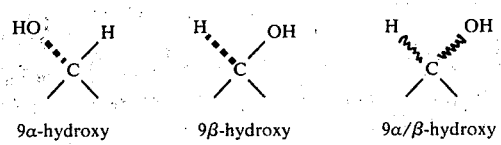

9α-hydroxy    9β-hydroxy    9α/β-hydroxy

The novel compounds of the present invention have utility as hypotensive agents, anti-ulcer agents, agents for the treatment of gastric hypersecretion and gastric erosion, bronchodilators, antimicrobial agents, anticonvulsants, abortifacients, agents for the induction of labor, agents for the induction of menses, fertility-controlling agents, central nervous system regulatory agents, analgesic agents, salt and water-retention regulatory agents, diuretics, fat metabolic regulatory agents, serum-cholesterol lowering agents, anti-inflammatory agents and as agents for the inhibition of platelet aggregation, and for the treatment of peridontal disease, glucoma, uveitis, sickle cell anemia and psoriasis. Certain of the novel compounds of this invention possess utility as intermediates for the preparation of other of the novel compounds of this invention.

The compounds of this invention also provide protection against the ulcerogenic properties of certain non-steroidal anti-inflammatory agents, e.g., indomethacin, aspirin, and phenylbutazone.

EXAMPLE 1

Preparation of
2-(6-carboxy-6-fluorohexyl)cyclopent-2-en-1-one

This cyclopentenone is prepared by the procedure described in Belgium Pat. No. 786,215 (Jan. 15, 1973) for the preparation of 2-(6-carboxyoctyl)cyclopent-2-en-1-one by substituting diethyl fluoromalonate for diethyl ethylmalonate.

EXAMPLE 2

Preparation of
2-(6-carboxy-6-phenylhexyl)cyclopent-2-en-1-one

This cyclopentenone is prepared by the procedure described in Belgium Pat. No. 786,215 (Jan. 15, 1973) for the preparation of 2-(6-carboxyoctyl)cyclopent-2-en-1-one by substituting diethyl phenylmalonate for diethyl ethylmalonate.

EXAMPLE 3

Preparation of
2-(6-carboxyheptyl)cyclopent-2-en-1-one

This cyclopentanone is prepared by the procedure described in Belgium Pat. No. 786,215 (Jan. 15, 1973) for the preparation of 2-(6-carboxyheptyl)cyclopent-2-en-1-one by substituting diethyl methyl malonate for diethyl ethylmalonate.

EXAMPLE 4

Preparation of
2-(6-carbo-n-butoxyhexyl)cyclopent-2-en-1-one

A solution of 50 g. of 2-(6-carboxyhexyl)cyclopent-2-en-1-one [Bagli et al., *Tetrahedron Letters*, No. 5, 465 (1966)] in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 5–7

Treatment of 2-(6-carboxyhexyl) cyclopent-2-en-1-one by the procedure of Example 4 with the appropriate alcohol affords the esters of the following table.

TABLE 1

| Example | Alcohol | Product Ester |
|---------|---------|---------------|
| 5 | Isopropanol | 2-(6-carboisopropoxy-hexyl)cyclopent-2-en-1-one |
| 6 | methanol | 2-(6-carbomethoxy-hexyl)cyclopent-2-en-1-one |
| 7 | 1-hydroxy-n-decane | 2-(6-carbo-n-decyloxy-hexyl)cyclopent-2-en-1-one |

EXAMPLE 8

Preparation of
4-bromo-2-(6-carboxyhexyl)cyclopent-2-en-1-one

A stirred mixture of 35.9 g. (0.171 moles) of 2-(6-carboxyhexyl)cyclopent-2-en-1-one [Bagli et al., Tetrahedron Letters, No. 5, 465 (1966)], 35.0 g. (0.197 moles) of N-bromosuccinimide, and 600 ml. of carbon tetrachloride is refluxed for 35 minutes. The mixture is cooled to 5° C. and filtered. The filtrate is washed with cold water, dried over magnesium sulfate, and taken to dryness to give an oil, $\lambda_{max}.^{MeOH}=225m\mu(8850)$; $\nu max.=1705$ (carbonyl groups) and 1625 cm$^{-1}$ (olefin group).

EXAMPLES 9–32

In the manner of the preceding Example 8, the various cyclopentenones of Table 1A, which follows, are converted to the corresponding 4-bromo derivatives.

TABLE 1A

| Example | Starting cyclopent-2-en-1-one | Product 4-Bromocyclopentenones |
|---------|-------------------------------|-------------------------------|
| 9 | 2-(6-carbethoxyhexyl)-cyclopent-2-en-1-one* | 4-bromo-2-(6-carbethoxyhexyl)-cyclopent-2-en-1-one |
| 10 | 2-(6-carbomethoxyhexyl)cyclopent-2-en-1-one (Example 6) | 4-bromo-2-(6-carbomethoxyhexyl)cyclopent-2-en-1-one |
| 11 | 2-(4-carbethoxybutyl)cyclopent-2-en-1-one* | 4-bromo-2-(4-carbethoxybutyl)cyclopent-2-en-1-one |
| 12 | 2-(3-carbethoxypropyl)cyclopent-2-en-1-one* | 4-bromo-2-(3-carbethoxypropyl)cyclopent-2-en-1-one |
| 13 | 2-(4-carboxybutyl)cyclopent-2-en-1-one* | 4-bromo-2-(4-carboxybutyl)cyclopent-2-en-1-one |
| 14 | 2-(3-carboxypropyl)cyclopent-2-en-one* | 4-bromo-2-(3-carboxypropyl)cyclopent-2-en-1-one |
| 15 | 2-(8carboxyoctyl)cyclopent-2-en-1-one* | 4-bromo-2-(8-carboxyoctyl)cyclopent-2-en-1-one |
| 16 | 2-(8-carbethoxyoctyl)cyclopent-2-en-1-one* | 4-bromo-2-(8-carbethoxyoctyl)cyclopent-2-en-1-one |
| 17 | 2-(6-carboxyoctyl)cyclopent-2-en-1-one* | 4-bromo-2-(6-carboxyoctyl)cyclopent-2-en-1-one |
| 18 | 2-(6-carbethoxyoctyl)cyclopent-2-en-1-one* | 4-bromo-2-(6-carbethoxyoctyl)cyclopent-2-en-1-one |
| 19 | 2-(6-carboxy-5,5-dimethylhexyl)cyclopent-2-en-1-one* | 4-bromo-2-(6-carboxy-5,5-dimethylhexyl)-cyclopent-2-en-1-one |
| 20 | 2-(6-carbethoxy-5,5-dimethylhexyl)cyclopent-2-en-1-one* | 4-bromo-2-(6-carbethoxy-5,5-dimethylhexyl)-cyclopent-2-en-1-one |
| 21 | 2-(6-carboxy-5- | 4-bromo-2-(6-carboxy-5- |

TABLE 1A-continued

| Example | Starting cyclopent-2-en-1-one | Product 4-Bromocyclopentenones |
|---|---|---|
| | oxahexyl)cyclopent-2-en-1-one* | oxahexyl)cyclopent-2-en-1-one |
| 22 | 2-(6-carbethoxy-5-oxahexyl)-cyclopent-2-en-1-one* | 4-bromo-2-(6-carbethoxy-5-oxahexyl)cyclopent-2-en-1-one |
| 23 | 2-(6-carboxy-6-fluorohexyl)-cyclopent-2-en-1-one (Example 1) | 4-bromo-2-(6-carboxy-6-fluorohexyl)cyclopent-2-en-1-one |
| 24 | 2-(5-carboxy-pentyl)cyclopent-2-en-1-one* | 4-bromo-2-(5-carboxy-pentyl)cyclopent-2-en-1-one |
| 25 | 2-(5-carbethoxy-pentyl)cyclopent-2-en-1-one* | 4-bromo-2-(5-carbethoxypentyl)cyclopent-2-en-1-one |
| 26 | 2-(7-carboxy-heptyl)cyclopent-2-en-1-one* | 4-bromo-2-(7-carboxy-heptyl)cyclopent-2-en-1-one |
| 27 | 2-(7-carbethoxy-heptyl)cyclopent-2-en-1-one* | 4-bromo-2-(7-carbethoxy-heptyl)cyclopent-2-en-1-one |
| 28 | 2-(6-carboxy-6-phenylhexyl)-cyclopent-2-en-1-one (Example 2) | 4-bromo-2-(6-carboxy-6-phenylhexyl)cyclopent-2-en-1-one |
| 29 | 2-(6-carbo-n-butoxyhexyl)-cyclpent-2-en-1-one (Example 4) | 4-bromo-2-(6-carbo-n-butoxyhexyl)cyclopent-2-en-1-one |
| 30 | 2-(6-carbo-iso-propoxyhexyl)-cyclo ent-2-en-1-one (Example 5) | 4-bromo-2-(6-carbo-isopropoxyhexyl)-cyclopent-2-en-1-one |
| 31 | 2-(6-carbo-n-decyloxyhexyl)-cyclopent-2-en-1-one (Example 7) | 4-bromo-2-(6-carbo-n-decyloxyhexyl)cyclopent-2-en-1-one |
| 32 | 2-(6-carboxy-heptyl)cyclopent-2-en-1-one (Example 3) | 4-bromo-2-(6-carboxy-heptyl)-cyclopent-2-en-1-one |

*Belgium Patent Number 786,215 (January 15, 1973).

EXAMPLE 33

Preparation of 4-methoxy-2-(6-carboxyhexyl)cyclopent-2-en-1-one

To a stirred solution of 5.30 g. of crude 4-bromo-2-(6-carboxyhexyl)cyclopent-2-en-1-one (Example 8) in 85ml. of methanol at 0°–3° C. is added 4.40 g. (22.6 mmole) of silver fluoborate in one portion. After 2 minutes, the mixture is treated with 2.66 g. (24.8 (mmoles) of 2,6-lutidine. After stirring for 30 minutes at 0°—3° C. the mixture is stirred at ambient temperature for 45 minutes. Silver bromide is removed by filtration, and the filtrate is concentrated to a volume of 40 ml. The solution is treated with saturated sodium chloride solution and extracted with ether. The extract is washed successively with 0.5 N hydrochloric acid solution, water, and saturated sodium chloride solution; dried over magnesium sulfate; and concentrated. Partition chromatography of the residue on Celite gives an oil, $\lambda_{max.}^{MeOH} = 220$ m$\mu$ (7450); $\nu$max.=1715 (carbonyl groups) and 1095 cm$^{-1}$ (methoxy group).

EXAMPLES 34–61

Alcoholysis with the appropriate alcohol of the 4-bromocyclopentenones listed in Table 2, directly following, in the manner of Example 33 provides the 4-alkoxycyclopentenones of the Table.

TABLE 2

| Example | Starting bromocyclopentenone of example | Product 4-alkoxycyclopent-2-en-1-one |
|---|---|---|
| 34 | 9 | 4-ethoxy-2-(6-carbethoxyhexyl)-cyclopent-2-en-1-one |
| 35 | 10 | 4-methoxy-2-(6-carbomethoxyhexyl)cyclopent-2-en-1-one |
| 36 | 11 | 4-propoxy-2-(4-carbethoxybutyl)-cyclopent-2-en-1-one |
| 37 | 12 | 4-isopropoxy-2-(3-carbethoxypropyl)cyclopent-2-en-1-one |
| 38 | 13 | 4-methoxy-2-(4-carboxybutyl)cyclopent-2-en-1-one |
| 39 | 14 | 4-ethoxy-2-(3-carboxypropyl)cyclopent-2-en-1-one |
| 40 | 15 | 4-methoxy-2-(8-carboxyoctyl)cyclopent-2-en-1-one |
| 41 | 16 | 4-isopropoxy-2-(8-carbethoxyoctyl)cyclopent-2-en-1-one |
| 42 | 17 | 4-methoxy-2-(6-carboxyoctyl)cyclopent-2-en-1-one |
| 43 | 18 | 4-n-butoxy-2-(6-carboxyoctyl)cyclopent-2-en-1-one |
| 44 | 19 | 4-methoxy-2-(6-carboxy-5,5-dimethylhexyl)-cyclopent-2-en-1-one |
| 45 | 20 | 4-methoxy-2-(6-carbethoxy-5,5-dimethylhexyl)cyclopent-2-en-1-one |
| 46 | 21 | 4-methoxy-2-(6-carboxy-5-oxahexyl)cyclopent-2-en-1-one |
| 47 | 22 | 4-ethoxy-2-(6-carbethoxy-5-oxahexyl)cyclopent-2-en-1-one |
| 48 | 23 | 4-methoxy-2-(6-carboxy-6-fluorohexyl)cyclopent-2-en-1-one |
| 49 | 24 | 4-methoxy-2-(5-carboxypentyl)cyclopent-2-en-1-one |
| 50 | 25 | 4-sec-butoxy-2-(5-carbethoxypentyl)cyclopent-2-en-1-one |
| 51 | 26 | 4-methoxy-2-(7-carboxyheptyl)cyclopent-2-en-1-one |
| 52 | 27 | 4-methoxy-2-(7-carbethoxyheptyl)cyclopent-2-en-1-one |
| 53 | 28 | 4-methoxy-2-(6-carboxy-6-phenylhexyl)cyclopent-2-en-1-one |
| 54 | 32 | 4-methoxy-2-(6-carboxy-heptyl)-cyclopent-2-en-1-one |
| 55 | 29 | 4-methoxy-2-(6-carbo-n-butoxyhexyl)cyclopent-2-en-1-one |
| 56 | 30 | 4-methoxy-2-(6-carbo-isopropoxyhexyl)cyclopent-2-en-1-one |
| 57 | 31 | 4-methoxy-2-(6-carbo-n-decyloxyhexyl)cyclopent-2-en-1-one |
| 58 | 8 | 4-ethoxy-2-(6-carboxyhexyl)cyclopent-2-en-1-one |
| 59 | 8 | 4-propoxy-2-(6-carboxy- |

TABLE 2-continued

| Example | Starting bromo-cyclopentenone of example | Product 4-alkoxycyclopent-2-en-1-one |
|---|---|---|
| | | hexyl)cyclopent-2-en-1-one |
| 60 | 8 | 4-isopropoxy-2-(6-carboxyhexyl)cyclopent-2-en-1-one |
| 61 | 8 | 4-n-butoxy-2-(6-carboxyhexyl)cyclopent-2-en-1-one |

EXAMPLE 62

Preparation of 4-tert-butoxy-2-(6-carbethoxyhexyl)cyclopent-2-en-1-one

A stirred mixture of 6.35 g. (20 mmoles) of 4-bromo-2-(carbethoxyhexyl)cyclopent-2-en-1-one (Example 9), 3.01 g. (11 moles) of silver carbonate, and 40 ml. of t-butanol is heated at 70° C. for 17 hours. The mixture is cooled and filtered. After evaporation of t-butanol the residue is treated with aqueous sodium chloride and extracted with 3:1 ether-hexane. The extract is washed with saturated sodium chloride solution, dried over magnesium sulfate, and concentrated. The crude product is purified by chromatography on silica gel to give in order of elution: the subject compound as an oil; $\lambda_{max.}^{MeOH} = 219$ m$\mu$ (8860); $\nu$max. = 1735 (ester carbonyl group), 1725 (ketone carbonyl group), and 1365 cm$^{-1}$ (tert.-butyl group); and 4-hydroxy-2-(6-carbethoxyhexyl)cyclopent-2-en-1-one also as an oil.

EXAMPLE 63

Preparation of 4-(2-hydroxyethoxy)-2-(6-carboxyhexyl)cyclopent-2-en-1-one

To a stirred solution of 19.1 g. of crude 4-bromo-2-(6-carboxyhexyl)cyclopent-2-en-1-one (Example 8) in 310 ml. of ethylene glycol is added 15.6 g. (80 mmole) of silver fluoborate during 2 minutes. The exothermic reaction is controlled to give a temperature of 29° C., and after 1 minute the mixture is treated during 1 minute with 8.6 g. ($\lambda$mmole) of 2,6-lutidine. The mixture is stirred at ambient temperature for 2 hours, diluted with water, and filtered. The filtrate is diluted with saturated sodium chloride solution and extracted with ether. The extract is washed with half-saturated sodium chloride solution containing a little hydrochloric acid and saturated sodium chloride solution. The extract is dried over magnesium sulfate and concentrated. Column chromatography of the residue on silica gel gives an oil, $\lambda_{max.}^{MeOH} = 216$ m$\mu$(8350); $\nu$max. = 3340 (hydroxyl groups), 1700 (carbonyl groups), and 1620 cm$^{-1}$ (olefin group).

EXAMPLES 64-85

By the procedure described in Example 63, treatment with the appropriate diol of the various 4-bromocyclopentenones listed in Table 3, which follows, are converted to the corresponding 4-($\omega$-hydroxyalkyl)cyclopentenones of the Table.

TABLE 3

| Example | Starting 4-bromo-cyclopentenone of Example | Product 4-($\omega$-hydroxyalkoxy)cyclopent-2-en-1-one |
|---|---|---|
| 64 | 11 9 | 4-$\beta$-hydroxyethoxy-2-(6-carbethoxyhexyl)cyclopent-2-en-1-one |
| 65 | 10 | 4-$\beta$-hydroxyethoxy-2-(6-carbomethoxyhexyl)cyclopent-2-en-1-one |
| 66 | 11 | 4-$\gamma$-hydroxypropoxy-2-(4-carbethoxybutyl)-cyclopent-2-en-1-one |
| 67 | 12 | 4-$\beta$-hydroxyethoxy-2-(3-carbethoxypropyl)cyclopent-2-en-1-one |
| 68 | 13 | 4-$\beta$-hydroxyethoxy-2-(4-carboxybutyl)cyclopent-2-en-1-one |
| 69 | 14 | 4-$\beta$-hydroxyethoxy-2-(3-carboxypropyl)cyclopent-2-en-1-one |
| 70 | 15 | 4-$\beta$-hydroxyethoxy-2-(8-carboxyoctyl)cyclopent-2-en-1-one |
| 71 | 16 | 4-$\beta$-hydroxyethoxy-2-(8-carbethoxyoctyl)cyclopent-2-en-1-one |
| 72 | 17 | 4-$\beta$-hydroxyethoxy-2-(6-carboxyoctyl)cyclopent-2-en-1-one |
| 73 | 18 | 4-$\gamma$-hydroxypropoxy-2-(6-carbethoxyoctyl)-cyclopent-2-en-1-one |
| 74 | 19 | 4-$\beta$-hydroxyethoxy-2-(6-carboxy-5,5-dimethyl-(hexyl)cyclopent-2-en-1-one |
| 75 | 20 | 4-$\beta$-hydroxyethoxy-2-(6-carbethoxy-5,5-dimethylhexyl)cyclopent-2-en-1-one |
| 76 | 21 | 4-$\beta$-hydroxyethoxy-2-(6-carboxy-5-oxahexyl)-cyclopent-2-en-1-one |
| 77 | 22 | 4-$\gamma$-hydroxypropoxy-2-(6-carbethoxy-5-oxahexyl)-cyclopent-2-en-1-one |
| 78 | 23 | 4-$\beta$-hydroxyethoxy-2-(6-carboxy-6-fluorohexyl)-cyclopent-2-en-1-one |
| 79 | 24 | 4-$\beta$-hydroxyethoxy-2-(5-carboxypentyl)cyclopent-2-en-1-one |
| 80 | 26 | 4-$\beta$-hydroxyethoxy-2-(7-carboxyheptyl)cyclopent-2-en-1-one |
| 81 | 28 | 4-$\beta$-hydroxyethoxy-2-(6-carboxy-6-phenylhexyl)-cyclopent-2-en-1-one |
| 82 | 29 | 4-$\beta$-hydroxyethoxy-2-(6-carbo-n-butoxyhexyl)-cyclopent-2-en-1-one |
| 83 | 30 | 4-$\beta$-hydroxyethoxy-2-(carboisopropoxyhexyl)-cyclopent-2-en-1-one |
| 84 | 31 | 4-$\beta$-hydroxyethoxy-2-(6-carbo-n-decyloxyhexyl)-cyclopent-2-en-1-one |
| 85 | 8 | 4-$\beta$-hydroxypropoxy-2-(6-carboxyhexyl)cyclopent-2-en-1-one |

EXAMPLE 86

Preparation of 4-$\beta$-tetrahydropyran-2'-yloxyethoxy-2-(6-carbotetrahydropyran-2'-yloxyhexyl)cyclopent-2-en-1-one To a stirred solution of 5.59 g. of 4-(2-hydroxyethoxy)-2-(6-carboxyhexyl)cyclopent-2-en-1-one (Example 63) and 20.7 g. (246 mmoles) of dihydropyran in 100 ml. of methylene chloride at 20° C. is added 47 mg. (0.246 mmoles) of p-toluenesulfonic acid monohydrate in one portion. The temperature is maintained at 20° C.-25° C. by cooling and is stirred for one hour at that temperature. The solution is diluted with 200 ml. of ether and poured into a mixture of 40 ml. of saturated sodium bicarbonate solution, 40 ml. of saturated sodium chloride solution, and 80 ml. of water. The phases are separated, and the aqueous phase is extracted with additional ether. The total extract is washed successively with water and saturated sodium chloride solution, dried over potassium carbonate, and freed of volatile matter by concentration at reduced pressure to give an oil, $\lambda_{max.}^{MeOH}=223$ m$\mu$ (9500); $\nu$max. 1730 (ester carbonyl group), 1705 (ketone carbonyl group), and 1030 cm$^{-1}$ (tetrahydropyranyloxy groups).

EXAMPLES 87-102

By the procedure described in Example 86 the 4-alkoxycyclopentenone carboxylic acids listed in Table 4 were converted to the corresponding tetrahydropyran-2'-yl esters of the table.

TABLE 4

| Example | Starting 4-alkoxycyclopentenone carboxylic acid of Example | Product Tetrahydropyran-2'yl ester 4-alkoxycyclopent-2-en-1-one |
|---|---|---|
| 87 | 38 | 4-methoxy-2-(4-carbotetrahydropyran-2'-yloxybutyl)cyclopent-2-en-1-one |
| 88 | 39 | 4-ethoxy-2-(3-carbotetrahydropyran-2'-yloxypropyl)cyclopent-2-en-1-one |
| 89 | 40 | 4-methoxy-2-(8-carbotetrahydropyran-2'-yloxyoctyl)cyclopent-2-en-1-one |
| 90 | 42 | 4-methoxy-2-(6-carbotetrahydropyran-2'-yloxyoctyl)cyclopent-2-en-1-one |
| 91 | 44 | 4-methoxy-2-(6-carbotetrahydropyran-2'-yloxy-5,5-dimethylhexyl)cyclopent-2-en-1-one |
| 92 | 46 | 4-methoxy-2-(6-carbotetrahydroxypyran-2'-yloxy-5-oxahexyl)cyclopent-2-en-1-one |
| 93 | 48 | 4-methoxy-2-(6-carbotetrahydropyran-2'-yloxy-6-fluorohexyl)cyclopent-2-en-1-one |
| 94 | 49 | 4-methoxy-2-(5-carbotetrahydropyran-2'-yloxypentyl)cyclopent-2-en-1-one |
| 95 | 51 | 4-methoxy-2-(7-carbotetrahydropyran-2'-yloxyheptyl)cyclopent-2-en-1-one |
| 96 | 53 | 4-methoxy-2-(6-carbotetrahydropyran-2'-yloxy-6-phenylhexyl)cyclopent-2-en-1-one |
| 97 | 58 | 4-ethoxy-2-(6-carbotetrahydropyran-2'-yloxyhexyl)cyclopent-2-en-1-one |
| 98 | 59 | 4-propoxy-2-(6-carbotetrahydropyran-2'-yloxyhexyl)cyclopent-2-en-1-one |
| 99 | 60 | 4-isopropoxy-2-(6-carbotetrahydropyran-2'-yloxyhexyl)cyclopent-2-en-1-one |
| 100 | 61 | 4-n-butoxy-2-(6-carbotetrahydropyran-2'-yloxyhexyl)cyclopent-2-en-1-one |
| 101 | 33 | 4-methoxy-2-(6-carbotetrahydropyran-2'-yloxyhexyl)cyclopent-2-en-1-one |
| 102 | 54 | 4-methoxy-2-(6-carbotetrahydropyran-2'-yloxyheptyl)cyclopent-2-en-1-one |

EXAMPLES 103-124

Treatment of the 4-($\omega$-hydroxyalkoxy)cyclopentenones of Table 5 below with dihydropyran in the manner of Example 86 provides the 4-($\omega$-tetrahydropyranyloxyalkoxy)cyclopentenone esters listed in the table.

TABLE 5

| Example | Starting 4-($\omega$-hydroxyalkoxy)-cyclopentenone of Example | Product 4-($\omega$-tetrahydropyran-2'-yloxyalkoxy)-cyclopent-2-en-1-one ester |
|---|---|---|
| 103 | 64 | 4-$\beta$-tetrahydropyrany-2'-yloxyethoxy-2-(6-carbethoxyhexyl)cyclopent-2-en-1-one |
| 104 | 65 | 4-$\beta$-tetrahydropyrany-2'-yloxyethoxy-2-(6-carbomethoxyhexyl)cyclopent-2-en-1-one |
| 105 | 66 | 4-$\gamma$-tetrahydropyran-2'-yloxypropoxy-2-(4-carbethoxybutyl)cyclopent-2-en-1-one |
| 106 | 67 | 4-$\beta$-tetrahydropyran-2'-yloxyethoxy-2-(3-carbethoxypropyl)cyclopent-2-en-1-one |
| 107 | 68 | 4-$\beta$-tetrahydropyran-2'-yloxyethoxy-2-(4-carbotetrahydropyran-2'-yloxybutyl)cyclopent-2-en-1-one |
| 108 | 69 | 4-$\beta$-tetrahydropyran-2'-yloxyethoxy-2-(3-carbotetrahydropyran-2'-yloxypropyl)cyclopent-2-en-1-one |
| 109 | 71 | 4-$\beta$-tetrahydropyran-2'-yloxyethoxy-2-(8-carbethoxyoctyl)cyclopent-2-en-1-one |
| 110 | 70 | 4-$\beta$-tetrahydropyran-2'-yloxyethoxy-2-(8-carbotetrahydropyran-2'-yloxyoctyl)cyclopent-2-en-1-one |
| 111 | 72 | 4-$\beta$-tetrahydropyran-2'-yloxyethoxy-2-(6-carbotetrahydropyran-2'-yloxyoctyl)cyclopent-2-en-1-one |
| 112 | 73 | 4-$\gamma$-tetrahydropyran-2'-yloxypropoxy-2-(6-carbethoxyoctyl)cyclopent-2-en-1-one |
| 113 | 74 | 4-$\beta$-tetrahydropyran-2'- |

TABLE 5-continued

| Example | Starting 4-(ω-hydroxyalkoxy)-cyclopentenone of Example | Product 4-(ω-tetrahydropyran-2'-yloxyalkoxy)-cyclopent-2-en-1-one ester |
|---|---|---|
| | | yloxyethoxy-2-(6-carbotetrahydropyran-2'-yloxy-5,5-dimethylhexyl)-cyclopent-2-en-1-one |
| 114 | 75 | 4-β-tetrahydropyran-2'-yloxyethoxy-2-(6-carbethoxy-5,5-dimethylhexyl)cyclopent-2-en-1-one |
| 115 | 76 | 4-β-tetrahydropyran-2'-yloxyethoxy-2-(6-carbotetrahydropyran-2'-yloxy-5-oxahexyl)cyclopent-2-en-1-one |
| 116 | 77 | 4-γ-tetrahydropyran-2'-yloxypropoxy-2-(6-carbethoxy-5-oxahexyl)cyclopent-2-en-1-one |
| 117 | 78 | 4-β-tetrahydropyran-2'-yloxyethoxy-2-(6-carbotetrahydropyran-2'-yloxy-6-fluorohexyl)cyclopent-2-en-1-one |
| 118 | 79 | 4-β-tetrahydropyran-2'-yloxyethoxy-2-(5-carbotetrahydropyran-2'-yloxypentyl)cyclopent-2-en-1-one |
| 119 | 80 | 4-β-tetrahydropyran-2'-yloxyethoxy-2-(7-carbotetrahydropyran-2'-yloxyheptyl)cyclopent-2-en-1-one |
| 120 | 81 | 4-β-tetrahydropyran-2'-yloxyethoxy-2-(6-carbotetrahydropyran-2'-yloxy-6-phenylhexyl)cyclopent-2-en-1-one |
| 121 | 82 | 4-β-tetrahydropyran-2'-yloxyethoxy-2-(6-carbo-n-butoxyhexyl)cyclopent-2-en-1-one |
| 122 | 83 | 4-β-tetrahydropyran-2'-yloxyethoxy-2-(6-carboisopropoxyhexyl)cyclopent-2-en-1-one |
| 123 | 84 | 4-β-tetrahydropyran-2'-yloxyethoxy-2-(6-carbo-n-decyloxyhexyl)cyclopent-2-en-1-one |
| 124 | 85 | 4-β-tetrahydropyran-2'-yloxypropoxy-2-(6-carbotetrahydropyran-2'-yloxyhexyl)cyclopent-2-en-1-one |

EXAMPLE 125

Preparation of 4-(4-hydroxybutoxy)-2-(6-carboxyhexyl)cyclopent-2-en-1-one

To a stirred solution of 56.0 g. of crude 4-bromo-2-(6-carboxyhexyl)cyclopent-2-en-1-one (Example 8) in 400 ml. of tetrahydrofuran and 133 ml. of water at 3° C. is added 44.1 g. (0.226 moles) of silver fluoborate during 25 minutes. The mixture is stirred at 0°–5° C. for 60 minutes, diluted with water and ether, and filtered. The aqueous portion of the filtrate is saturated with solid sodium chloride and extracted with additional ether. The combined organic phases are washed successively with water and saturated sodium chloride solution, dried over magnesium sulfate, and concentrated. Column chromatography of the residue gives the subject compound as a mixture with 4-hydroxy-2-(6-carboxyhexyl)cyclopent-2-en-1-one, NMR(CDCl$_3$) 3.60 (multiplet, O-methylene hydrogens) and 4.60 (multiplet, O-methine hydrogen).

EXAMPLE 126

Preparation of 4-(4-tetrahydropyranoloxybutoxy)-2-(6-tetrahydropyranylcarboxyhexyl)cyclopent-2-en-1-one In the manner of Example 86 the mixture of 4-hydroxy-2-(6-carboxyhexyl)cyclopent-2-en-1-one and 4-(4-hydroxybutoxy)-2-(6-carboxyhexyl)cyclopent-2-en-1-one (Example 125) is converted to a mixture of the subject compound and 4-tetrahydropyranyloxy-2-(6-tetrahydropyranylcarboxyhexyl)cyclopent-2-en-1-one with dihydropyran and p-toluenesulfonic acid monohydrate in methylene chloride.

EXAMPLE 127

Preparation of 3-triphenylmethoxy-1-octyne

A mixture of 1.26 g. (10.0 mmoles) of 1-octyn-3-ol, 4.85 g. (15.0 mmoles) of triphenylmethyl bromide, and 50 ml. of dry pyridine is heated at 95° C. for 60 minutes with occasional swirling. The solution is cooled, treated with water, and extracted with ether. The extract is washed successively with water and saturated sodium chloride, dried over magnesium sulfate, and concentrated. The crude product is purified by chromatography on Florisil and recrystallization from petroleum ether to give white crystals, m.p. 65°–66° C. λ max. (KBr) 3280 (acetylenic hydrogen), 1605, 1030, and 702 cm$^{-1}$ (triphenylmethoxy group).

EXAMPLE 128

Preparation of 1-iodo-3-triphenylmethoxy-trans-1-octene

To a mixture of 0.650 g. (16.91 mmole) of sodium borohydride and 3.17 g. (45.2 mmoles) of 2-methyl-2-butene in 40 ml. of diglyme cooled to −5° C. under an inert atmosphere is added over 15 minutes 3.24 g. (22.6 mmoles) of boron trifluoride etherate and the resulting mixture is stirred at 0° C. for 2 hours. To this mixture is then added over 5 minutes 8.32 g. (22.6 mmoles) of 3-triphenylmethoxyl-1-octyne (Example 127) in 10 ml. diglyme, the cooling bath is removed, and the mixture is stirred at ambient temperature for 1.5 hours. The mixture is cooled to 0° C. and 6.0 g. of finely divided anhydrous trimethylamine oxide is added over 10 minutes. The cooling bath is removed and the mixture is stirred at ambient temperatures for 0.5 hour. The mixture is then poured into 200 ml. of 15% sodium hydroxide solution, a solution of 16 g. (63 mmoles) of iodine in 20 ml. of tetrahydrofuran is added immediately, and the resulting mixture is stirred for 0.5 hour. The organic phase is separated and the aqueous phase is washed with ether. The combined organic phase and washings are decolorized with 5% sodium thiosulfate solution, washed with saturated brine, dried (Na$_2$SO$_4$), and evaporated. The residue is dry-columned chromatographed upon alumina using hexane as eluent and the title compound is isolated as an oil.

EXAMPLES 129–138

In accordance with the method described in Example 127, the various 3-hydroxy-1-alkynes listed in Table 6 below are converted to the corresponding 3-triphenylmethoxy-1-alkynes by treatment with triphenylmethyl bromide.

TABLE 6

| Example | Starting 3-hydroxy-1-alkyne | Product 3-triphenylmethoxy-1-alkyne |
|---|---|---|
| 129 | 1-heptyn-3-ol | 3-triphenylmethoxyheptyne-1 |
| 130 | 1-hexyn-3-ol | 3-triphenylmethoxyhexyne-1 |
| 131 | 1-pentyn-3-ol | 3-triphenylmethoxypentyne-1 |
| 132 | 1-nonyne-3-ol[a] | 3-triphenylmethoxynonyne-1 |
| 133 | 1-decyne-3-ol[b] | 3-triphenylmethoxydecyne-1 |
| 134 | 4-ethyl-1-octyne-3-ol | 3-triphenylmethoxy-4-ethyl-octyne-1 |
| 135 | 4-methyl-1-heptyne-3-ol | 3-triphenylmethoxy-4-methylheptyne-1 |
| 136 | 7-methyl-6-en-1-octyne-3-ol[c] | 3-triphenylmethoxy-7-methyl-6-en-octyne-1 |
| 137 | 5,9-dimethyl-9-en-1-decyne-3-ol[d] | 3-triphenylmethoxy-5,9-dimethyl-9-en-decyne-1 |
| 138 | cis-5-en-1-octyne-3-ol[e] | 3-triphenylmethoxy-cis-5-en-octyne-1 |

References:
[a] M. Bertrand, Bull. Soc. Chim. France, 461 (1956).
[b] F. Bohlmann and D. Ratz, Chem. Ber., 90, 2265 (1957).
[c] U.S. Pat. No. 3,452,105 (June 24, 1969); Chem. Abs., 71, 60678 (1969).
[d] Sequin, Bull. Soc. Chim. France, 12, 948 (1945).
[e] J. Fried et al., Jour. Amer. Chem. Soc., 94, 4342 (1972).

EXAMPLE 138A

Preparation of 3-methoxy-1-octyne

To an ice-cooled solution of 63 g. of 1-octyne-3-ol in 300 ml. of dimethoxyethane is added under an inert atmosphere 312 ml. of 1.6 M n-butyllithium in hexane dropwise over 1 hour. To the mixture is then added 145 g. of methyl iodide and the resulting mixture is stirred at ambient temperatures for 24 hours and then heated to 60° C. for 1 hour. The mixture is cooled and poured into cold dilute hydrochloric acid. The organic phase is separated, washed with water and saturated brine, dried ($Na_2SO_4$), and evaporated to an oil, dried ($Na_2SO_4$), and evaporated to an oil. Fractional distillation of the oil in vacuo yields the product as a colorless oil.

EXAMPLES 139–148

Treatment of the 1-alkynes listed in Table 7 below with disiamylborane (prepared in situ from 2-methyl-2-butene, sodium borohydride and boron trifluoride), trimethylamine oxxide, iodine and aqueous sodium hydroxide by the procedure described in Example 128 furnishes the product 3-triphenylmethoxy-1-iodo-trans-1-alkenes of the Table.

TABLE 7

| Example | Starting 1-alkyne of Example | Product 1-iodo-trans-1-alkene |
|---|---|---|
| 139 | 129 | 1-iodo-3-triphenylmethoxy-trans-1-heptene |
| 140 | 130 | 1-iodo-3-triphenylmethoxy-trans-1-hexene |
| 141 | 131 | 1-iodo-3-triphenylmethoxy-trans-1-pentene |
| 142 | 132 | 1-iodo-3-triphenylmethoxy-trans-1-nonene |
| 143 | 133 | 1-iodo-3-triphenylmethoxy-trans-1-decene |
| 144 | 134 | 1-iodo-3-triphenylmethoxy-4-ethyl-trans-1-octene |
| 145 | 135 | 1-iodo-3-triphenylmethoxy-4-methyl-trans-1-heptene |
| 146 | 136 | 1-iodo-3-triphenylmethoxy-7-methyl-trans-1,6-octadiene |
| 147 | 137 | 1-iodo-3-triphenylmethoxy-5,9-dimethyl-trans-1,9-decadiene |
| 148 | 138 | 1-iodo-3-triphenylmethoxy-trans-1,cis-5-octadiene |
| 148A | 138A | 1-iodo-3-methoxy-trans-1-octene |

EXAMPLE 149

Preparation of 4,4-dimethyl-1-octyn-3-ol

To a solution of 20.2 g. (0.220 mole) of lithium acetylide-ethylenediamine complex in 100 ml. of dry dimethylsulfoxide is added 25.6 g. (0.200 mole) of 2,2-dimethyl-1-hexanal, prepared according to the procedure of G. Stork and S. R. Dowd, J. Amer. Chem. Soc., 85, 2178 (1963), in 25 ml. of dimethylsulfoxide at a rate to maintain a temperature of 25° C. (cooling). The mixture is then maintained at 25° C. for 2 hours and is poured onto ice and excess hydrochloric acid. The mixture is extracted with ether and the organic phase is washed with water and saturated brine, dried ($Na_2SO_4$), and evaporated to an oil. Distillation in vacuo yields the product as a colorless oil.

EXAMPLE 150

Preparation of 4,4-dimethyl-3-tetrahydropyranyloxy-1-octyne

To a solution of 23.1 g. (0.150 mole) of 4,4-dimethyl-1-octyn-3-ol (Example 149) in 126 g. of freshly distilled dihydropyran is added 1 drop of phosphorus oxychloride and the solution is maintained at ambient temperature in a tightly stoppered flask for 20 hours. Five drops of triethylamine are then added and the mixture is evaporated in vacuo to an oil. The oil is chromatographed on 600 g. of silica gel and the product is eluted with 5% ethyl acetate in benzene yielding a colorless oil.

EXAMPLE 151

Preparation of 4,4-dimethyl-1-iodo-trans-1-octen-3-ol

To 233 ml. of a 0.43N solution of disiamylborane in diglyme cooled to 0° C. under an inert atmosphere is added 23.8 g. (0.100 mole) 4,4-dimethyl-3-tetrahydropyranyloxy-1-octyne (Example 150). The mixture is allowed to come to room temperature and is stirred at ambient temperature for 3 hours. The solution is cooled to 0° C. and 22.5 g. (0.30 mole) of triethylamine oxide is added portionwise such that the temperature is maintained at 0°–5° C. The mixture is stirred at 0° C. for 1 hour and is then poured into 150 ml. of 1N sodium hydroxide followed immediately by a solution of 25.4 g. (0.100 mole) of iodine in 60 ml. of tetrahydrofuran. The mixture is stirred at ambient temperatures for 0.5 hour and poured into 500 ml. of water. The mixture is decolorized by addition of sodium thiosulfate and is extracted into ether. The organic phase is washed with water and the solvent is removed in vacuo. The residue is stirred at room temperature for 20 hours with 900 ml. 3:1:1 tetrahydrofuran-acetic acid-water. The solution is evaporated in vacuo and the residue is chromatographed on silica gel in benzene using 10–20% ethylacetate in benzene.

EXAMPLE 152

Preparation of 4,4-dimethyl-1-iodo-3-triphenylmethoxy-trans-1-octene

Treatment of 11.2 g. (0.396 mole) of 4,4-dimethyl-1-iodo-trans-1-octen-3-ol (Example 151) with 12.8 g. of triphenylmethyl bromide in 50 ml. of pyridine and purification on Florisil ®, all as described in Example 127 gives the title compound.

EXAMPLE 153

Preparation of 5,5-dimethyl-1-octyn-3-ol

Treatment of 20.2 g. (0.220 mole) of lithium acetylide-ethylenediame complex in 100 ml. of dimethylsulfoxide with 25.6 g. (0.200 mole) of 3,3-dimethylhexanol [prepared according to the procedure of A. W. Burgstahler, J. Amer. Chem. Soc., 82, 4681 (1960)] and distilation of the product, all as described in Example 149 yields the title compound.

EXAMPLE 154

Preparation of 5,5-dimethyl-3-tetrahydropyranyloxy-1-octyne

Treatment of 23.1 g. (0.150 mole) of 5,5-dimethyl-1-octyne-3-ol (Example 153) with 126 g. of dihydropyran and 1 drop of phosphorus oxychloride as described in Example 150 gives the title compound.

EXAMPLE 155

Preparation of 5,5-dimethyl-1-iodo-trans-octen-3-ol

Treatment of 23.8 g. (0.100 mole) of 5,5-dimethyl-3-tetrahydropyranyloxy-1-octyne (Example 154) successively with 233 mg. of 0.43M disiamylborane in diglyme, 22.5 g. of trimethylamine oxide, 150 ml. of 1N sodium hydroxide, 25.4 g. of iodine, and 900 ml. of 3:1:1 tetrahydrofuran-acetic acid-water as described in Example 151 gives the title compound.

EXAMPLE 156

Preparation of 5,5-dimethyl-1-iodo-3-triphenylmethoxy-trans-1-octene

Treatment of 6.0 g. of 5,5-dimethyl-1-iodo-trans-1-octen-3-ol (Example 155) with 6.9 g. of triphenylmethyl bromide in 30 ml. of pyridine and purification on Florisil ®, all as described in Example 127 gives the title compound.

EXAMPLE 157

Preparation of 1,1-dimethoxy-cis-3,4-methanohexane (cis-1-ethyl-2-(2,2-dimethoxyethyl)-cyclopropane)

To an ethereal suspension of zinc-silver couple, prepared according to the procedure of J. M. Danis, C. Girand, and J. M. Conia, Synthesis, 1972, 549, from 0.400 g. of silver acetate, 400 ml. of acetic acid, 68 g. of granular zinc, silver wool, and 600 ml. of ether, is added dropwise 136 g. of diiodomethane at a rate to maintain a gentle reflux. The mixture is then stirred at room temperature for 1 hour and to it is then added 57.7 g. of 1,1-dimethoxy-cis-3-hexane (M. Winter, Helvetica Chimica Acta, 46, 1792 (1963)) over a period of 20 minutes and the mixture is refluxed for 5 hours. The mixture is cooled to 0° C., 600 ml. of ether is added followed by 50.5 g. of pyridine dropwise over a period of 1 hour. The resulting precipitate is filtered and washed with ether. The filtrate and washings are combined and evaporated and the residue is fractionally distilled at 12 torr. to yield the title compound as a colorless oil.

EXAMPLE 158

Preparation of cis-3,4-methano-1-hexanol

To a vigorously stirred solution of 31.6 g. of 1,1-dimethoxy-cis-3,4-methano-hexane (Example 157), 75 mg. of hydroquinone, 6 g. of oxalic acid in 150 ml. of acetone heated at 45° C. under an inert atmosphere is added 700 ml. of water over a period of 0.5 hour. The mixture is cooled and extracted well with either. The organic phase is separated, washed with saturated sodium bicarbonate solution and saturated brine, dried ($Na_2SO_4$) and evaporated. The residue is distilled at 30 torr. to yield the title compound.

EXAMPLE 159

Preparation of cis-5,6-methano-1-octyn-3-ol

To a solution of 15.2 g. (0.165 mole) of lithium acetylide-ethylenediamine complex in 100 ml. of dry dimethylsulfoxide is added 16.8 g. (0.150 mole) of cis-3,4-methano-1-hexanol (Example 158) in 25 ml. of dimethylsulfoxide at a rate to maintain a temperature of 25° C. (cooling). The mixture is then maintained at 25° C. for 2 hours and is poured onto ice and excess hydrochloric acid. The mixture is extracted with ether and the organic phase is washed with water and saturated brine, dried ($Na_2SO_4$), and evaporated to an oil. Distillation in vacuo yields the title compound as a colorless oil.

EXAMPLE 160

Preparation of 3-triphenylmethoxy-cis-5,6-methano-1-octyne

A mixture of 13.8 g. of cis-5,6-methano-1-octyn-3-ol (Example 159) and 33.0 g. of triphenylmethyl bromide in 100 ml. of pyridine is heated to 100° C. for 1.5 hours under an inert atmosphere. The mixture is cooled and filtered. The filtrate is partitioned between ice water and ether. The organic phase is washed with cold dilute hydrochloric acid, saturated sodium bicarbonate solution, and saturated brine, dried ($Na_2SO_4$), and evaporated to an oil. The latter is dissolved in hexane and passed to an oil. The latter is dissolved in hexane and passed through 400 g. of Florisil ® to yield after evaporation the title compound as a colorless oil.

EXAMPLE 161

Preparation of 1-iodo-3-triphenylmethoxy-cis-5,6-methano-trans-1-octene

To 160 ml. of a 0.50M solution of disiamylborane in diglyme cooled to 0° C. under an inert atmosphere is added 28.6 g. (0.075 mole) 3-triphenylmethoxy-cis-5,6-methano-1-octyne (Example 160). The mixture is allowed to come to room temperature and is stirred at ambient temperature for 3 hours. The solution is cooled to 0° C. and 16.9 g. (0.225 mole) of triethylamine oxide is added portionwise such that the temperature is maintained at 0°–5° C. The mixture is stirred at 0° C. for 1 hour and is then poured into 300 ml. of 1 N sodium hydroxide followed immediately by a solution of 57 g. (0.225 mole) of iodine in 150 ml. of tetrahydrofuran. The mixture is stirred at ambient temperatures for 0.5 hour and poured into 1000 ml. of water. The mixture is decolorized by addition of sodium thiosulfate solution and is extracted into ether. The organic phase is washed with water and the solvent is removed in vacuo. The residue is purified by dry-column chromatography upon 1.5 kg. of alumina using hexane as eluent. The title compound is obtained as an oil.

EXAMPLES 162–168

Treatment of the carboxaldehydes listed in Table 8 below with lithium acetylide by the procedure described in Example 159 followed by treatment of the resulting 3-hydroxy-1-alkyne with triphenylmethyl bromide by the procedure of Example 160 furnishes the product 3-triphenylmethoxy-1-alkynes of the table.

TABLE 8

| Example | Starting carboxaldehyde | Product 3-triphenylmethoxy-1-alkyne |
|---|---|---|
| 162 | (2-cyclohexenyl)-acetaldehyde[1] | 4-(2-cyclohexenyl)-3-triphenylmethoxy-1-butyne |
| 163 | (3-cyclohexenyl)-acetaldehyde[1] | 4-(3-cyclohexenyl)-3-triphenylmethoxy-1-butyne |
| 164 | adamantane-1-carboxaldehyde | 3-(1-adamantyl)-3-triphenylmethoxy-1-propyne |
| 165 | 2-cyclohexene-carboxaldehyde | 3-(2-cyclohexenyl)-3-triphenylmethoxy-1-propyne |
| 166 | 3-cyclohexene-carboxaldehyde | 3-(3-cyclohexenyl)-3-triphenylmethoxy-1-propyne |
| 167 | adamantane-2-carboxaldehyde[2] | 3-(2-adamantyl)-3-triphenylmethoxy-1-propyne |
| 168 | (adamantyl-1)acetaldehyde | 4-(1-adamantyl)-1-butyne |

[1] C. W. Whitehead et al., J. Org. Chem., 26, 2814 (1961)
[2] A. H. Alberto, H. Wynberg and J. Strating, Synthetic Communications, 2, 79 (1972)

EXAMPLES 169–175

Treatment of the 3-triphenylmethoxy-1-alkynes listed in Table 9 below with disiamylborane, trimethylamine oxide, iodine and aqueous sodium hydroxide by the procedure described in Example 161 furnishes the product 3-triphenylmethoxy-1-iodo-1-trans-alkenes of the table.

TABLE 9

| Example | Starting 3-triphenylmethoxy-1-alkynes of Example | Product 3-triphenylmethoxy-1-iodo-1-trans-alkene |
|---|---|---|
| 169 | 162 | 4-(2-cyclohexenyl)-3-triphenylmethoxy-1-iodo-1-trans-butene |
| 170 | 163 | 4-(3-cyclohexenyl)-3-triphenylmethoxy-1-iodo-1-trans-butene |
| 171 | 164 | 3-(1-adamantyl)-3-triphenylmethoxy-1-iodo-1-trans-propene |
| 172 | 165 | 3-(2-cyclohexenyl)-3-triphenylmethoxy-1-iodo-1-trans-propene |
| 173 | 166 | 3-(3-cyclohexenyl)-3-triphenylmethoxy-1-iodo-1-trans-propene |
| 174 | 167 | 3-(2-adamantyl)-3-triphenylmethoxy-1-iodo-1-trans-propene |
| 175 | 168 | 4-(1-adamantyl)-3-triphenylmethoxy-1-iodo-1-trans-butene |

EXAMPLE 176

Preparation of cyclopentylacetyl chloride

To a solution of 50 g. of cyclopentaneacetic acid containing 2.9 ml. of N,N-dimethylformamide is added dropwise, with stirring, 51 g. of thionyl chloride over a period of 15 minutes. After stirring for an additional 60 minutes excess thionyl chloride is removed in vacuo and the residual oil is distilled to give 55.4 g. (97%) of product, b.p. 57°–58° C. (10 mm.).

EXAMPLE 177

Preparation of 1-chloro-4-cyclopentyl-1-trans-buten-3-one

A three-necked flask filtered with a stirrer, a gas inlet tube and a gas outlet tube protected with a calcium chloride tube is surrounded by an ice-water bath. The system is flushed with acetylene for 3 minutes. Carbon tetrachloride (150 ml.) is added to the flask and acetylene is bubbled through at a fast rate for 3 minutes. Aluminum chloride (59 g.) is added and actylene is bubbled through the mixture for 5 minutes. The gas inlet tube is replaced by a dropping funnel protected by a calcium chloride drying tube. Cyclopentaneacetyl chloride (55.4 g., Example 176) is added to the reaction mixture with stirring over a period of about 20 minutes. The dropping funnel is replaced by the gas inlet tube and with stirring, acetylene gas is bubbled through at a rate in excess of the saturation rate. After about 15 minutes the rate of absorption of acetylene suddenly becomes very rapid, and the acetylene is passed through as rapidly as it is absorbed. The introduction of acetylene is continued for 45 minutes after rapid absorption (which lasts about 1 hour) has subsided.

The reaction mixture is poured with stirring onto 430 g. of ice + 180 ml. of saturated sodium chloride solution. The aqueous phase is extracted three times more with ether. The combined extracts are dried with anhydrous magnesium sulfate and evaporated to dryness in vacuo. After addition of 1.5 g. of hydroquinone the residual oil is distilled to give 57 g. (89%) of oil, b.p. 67°–69° C. (0.14 mm.).

EXAMPLE 178

Preparation of 45-cyclopentyl-1-iodo-1-trans-buten-3-one

A solution of 57 g. of 1-chloro-4-cyclopentyl-1-trans-butene-3-one (Example 177) in 36.0 ml. of acetone containing 55 g. of sodium iodide is stirred at the reflux temperature for 18 hours. The resulting mixture is cooled, filtered and the mother liquor is taken to dryness. The residual oil is dissolved in ether washed successively with water, dilute sodium thiosulfate solution, and saturated sodium chloride solution, dried with anhydrous magnesium sulfate and taken to dryness to give 87 g. (99%) of orange oil. Vapor phase chromatography shows one peak.

EXAMPLE 179

Preparation of 4-cyclopentyl-1iodo-1-trans-buten-3-ol

To a solution of 7.1 g. of sodium borohydride in 60 ml. of absolute alcohol, stirred in an ice bath under nitrogen atmosphere, is added dropwise, over a period of about 2 hours, a solution containing 87 g. of 4-cyclopentyl-1-iodo-trans-buten-3-one (Example 178) in 160 ml. of absolute alcohol. The temperature is maintained at 5°–10° C. The solution is poured into 850 ml. of ice water and the resulting mixture is extracted three times with ether. The combined extracts are washed with dilute sodium bisulfite solution, saturated sodium chloride solution, dried with anhydrous magnesium sulfate and taken to dryness to give 81 g. of yellow oil. Column chromatography on a column of 1 kg. of silica gel using benzene as elute gives 75 g. (88%) of oily product.

EXAMPLES 180–199

Treatment of the listed carboxylic acids in Table 10 below with thionyl chloride by the procedure described in Example 176 followed by treatment of the resulting acid chloride with acetylene by the procedure described in Example 177, and thence by treatment of the resulting 1-chloro-1-trans-alkene-3-one with sodium iodide by the procedure described in Example 178, and then by treatment of the resulting 1-iodo--trans-alkene-3-one with sodium borohydride by the procedure described in Example 179 is productive of the product 3-hydroxy-1-iodo-1-trans-alkenes of the table.

TABLE 10

| Example | Starting carboxylic acid | Product 3-hydroxy-1-iodo-1-trans-alkene |
|---|---|---|
| 180 | cyclobutylacetic acid[1] | 4-cyclobutyl-3-hydroxy 1-iodo-1-trans-butene |
| 181 | 3-cyclopentylpropionic acid | 5-cyclopentyl-3-hydroxy-1-iodo-1-trans-pentene |
| 182 | 4-cyclopentylbutyric acid[2] | 6-cyclopentyl-3-hydroxy-1-iodo-1-trans-hexene |
| 183 | 5-cyclopentylpentanoic acid[2] | 7-cyclopentyl-3-hydroxy-1-iodo-1-trans-heptene |
| 184 | 6-cyclopentylhexanoic acid[2] | 8-cyclopentyl-3-hydroxy-1-iodo-1-trans-octene |
| 185 | 2-methyl-3-cyclopentylpropanoic acid[3] | 5-cyclopentyl-4-methyl-3-hydroxy-1-iodo-1-trans-pentene |
| 186 | 2-ethyl-4-cyclopentylbutyric acid[4] | 6-cyclopentyl-4-ethyl-3-hydroxy-1-iodo-1-trans-hexene |
| 187 | (2-trans-methylcyclopentyl)-acetic acid[5] | 4-(2-trans-methylcyclopentyl)-3-hydroxy-1-iodo-1-trans-butene |
| 188 | cyclohexylacetic acid | 4-cyclohexyl-3-hydroxy-1-iodo-1-trans-butene |
| 189 | 3-cyclohexylpropionic acid | 5-cyclohexyl-3-hydroxy-1-iodo-1-trans-pentene |
| 190 | 4-cyclohexylbutyric acid[6] | 6-cyclohexyl-3-hydroxy-1-iodo-1-trans-hexene |
| 191 | cycloheptylacetic acid[7] | 4-cycloheptyl-3-hydroxy-1-iodo-trans-butene |
| 192 | cyclooctylacetic acid[8,9] | 4-cyclooctyl-3-hydroxy-1-iodo-1-trans-butene |
| 193 | (4-methylcyclohexyl)acetic acid[10] | 4-(4-methylcyclohexyl)-3-hydroxy-1-iodo-1-trans-butene |
| 194 | (3-methylcyclohexyl)acetic acid[11] | 4-(3-methylcyclohexyl)-3-hydroxy-1-iodo-1-trans-butene |
| 195 | trans-2-methylcyclopentane carboxylic acid[12] | 3-(trans-2-methylcyclopentyl)-3-hydroxy-1-iodo-1-trans-propene |
| 196 | cyclohexane carboxylic acid | 3-cyclohexyl-3-hydroxy-1-iodo-1-trans-propene |
| 197 | trans-4-methylcyclohexane carboxylic acid[13] | 3-(trans-4-methylcyclohexyl)-3-hydroxy-1-iodo-1-trans-propene |
| 198 | cyclooctane carboxylic acid[14] | 3-cyclooctyl-3-hydroxy-1-iodo-1-trans-propene |
| 199 | cycloheptane carboxylic acid | 3-cycloheptyl-3-hydroxy-1-iodo-1-trans-propene |

References Table 10)
[1] C. G. Overberger et al., J. Polymer Sci., P&A; 2, 755 (1964).
[2] M. I. Goryeav et al., Chem. Abs., 69, 1742, No. 186462 (1968).
[3] C. D. Nenizescu and G. C. Vantu, Bull. Soc. Chim. France [5], 2, 2209 (1935).
[4] G. R. Yoke and R. Adams, J. Amer. Chem. Soc., 50, 1503 (1928).
[5] W. Herz, J. Org. Chem., 20, 1062 (1955).
[6] G. S. Hien and R. Adams, J. Amer. Chem. Soc., 48, 2385 (1926).
[7] E. E. Royals and A. N. Neal, J. Org. Chem., 21, 1448 (1956).
[8] F. F. Blicke and W. K. Johnson, J. Am. Pharm. Assoc. Sci. Ed., 45, 443 (1956).
[9] L. Ruzicka and H. A. Boekenogen, Helv. Chim. Acta, 14, 1319 (1931).
[10] A. N. Burgstahler and I. C. Nordin, J. Amer. Chim. Soc., 83, 198 (1961).
[11] J. von Braun and W. Teuffert, Ber., 58B, 2210 (1925).
[12] M. Julia and F. LeGaffic, Bull. Soc., Chim. Fr., 1550 (1965).
[13] V. N. Ipatieff et al., J. Amer. Chem. Soc., 75, 6222 (1953).
[14] A. T. Blomquist and F. W. Schlaefer, J. Amer. Chem. Soc., 83, 4547 (1961).

EXAMPLE 200

Preparation of 4-cyclopentyl-1-iodo-3-triphenylmethoxy-1-trans-butene

A mixture of 21.4 g. of 4-cyclopentyl-1-iodo-1-trans-buten-3-ol (Example 179) in 170 ml. of dry pyridine containing 31 g. of triphenylmethyl bromide is heated on the steam-bath for 2 hours. The dark mixture is poured into 850 ml. of iced water and the resulting solution is extracted three times with ether. The combined extracts are washed with ice cold 2% hydrochloric acid until the washings are acidic, saturated sodium chloride solution, dried with anhydrous magnesium sulfate and taken to dryness. Trituration of the residue followed by filtration removes triphenylcarbinol. The mother liquor is taken to dryness and the residual syrup is chromatographed on 400 g. of florisil using hexane gives 32 g. (78%) of syrup which solidifies on standing. Recrystallization from hexane affords white crystals, m.p. 87°–88° C.

EXAMPLE 201

Preparation of 4-cyclopentyl-1-iodo-3-(p-methoxyphenyldiphenyl)methoxy-1-trans-butene A solution of 20 g. of 4-cyclopentyl-1-iodo-1-trans-buten-3-ol (Example 179) and 25 g. of p-anisylchlorodiphenylmethane in 170 ml. of dry pyridine is kept at 60° C. for 18 hours, then at 70° C. for 3 hours. The cooled solution is poured into 850 ml. of iced water. The resulting solution is partitioned between ether and water. The ether layer is wahsed with water, dried with anhydrous magnesium sulfate and taken to dryness. Further evaporation with toluene gets rid of residual pyridine. The resulting oil is chromatographed on 300 g. of florisil with hexanes to give 22.3 g. of product. The material is homogeneous according to thin layer chromatography.

EXAMPLES 202-221

Treatment of the listed 3-hydroxy-1-iodo-trans-1-alkenes of Table 11 below with triphenylmethylbromide by the procedure described in Example 200 above is productive of the product 3-triphenylmethoxy-1-iodo-trans-1-alkenes of the table.

TABLE 11

| Example | Starting 1-iodo-1-trans-alkene of Example | Product 3-triphenyl-methoxy-1-iodo-trans-1-alkene |
|---|---|---|
| 202 | 180 | 4-cyclobutyl-3-triphenylmethoxy-1-iodo-1-trans-butene |
| 203 | 181 | 5-cyclopentyl-3-triphenylmethoxy-1-iodo-1-trans-pentene |
| 204 | 182 | 6-cyclopentyl-3-triphenylmethoxy-1-iodo-1-trans-hexene |
| 205 | 183 | 7-cyclopentyl-3-triphenylmethoxy-1-iodo-1-trans-heptene |
| 206 | 184 | 8-cyclopentyl-3-triphenylmethoxy-1-iodo-1-trans-octene |
| 207 | 185 | 5-cyclopenyl-4-methyl-3-triphenylmethoxy-1-iodo-1-trans-pentene |
| 208 | 186 | 6-cyclopentyl-4-ethyl-3-triphenylmethoxy-1-iodo-1-trans-hexene |
| 209 | 187 | 4-(2-trans-methylcyclopentyl)-3-triphenylmethoxy-1-iodo-1-trans-butene |
| 210 | 188 | 4-cyclohexyl-3-triphenylmethoxy-1-iodo-1-trans-butene |
| 211 | 189 | 5-cyclohexyl-3-triphenylmethoxy-1-iodo-1-trans-pentene |
| 212 | 190 | 6-cyclohexyl-3-triphenylmethoxy-1-iodo-1-trans-hexene |
| 213 | 191 | 4-cycloheptyl-3-triphenylmethoxy-1-iodo-1-trans-butene |
| 214 | 192 | 4-cyclooctyl-3-triphenylmethoxy-1-iodo-1-trans-butene |
| 215 | 193 | 4-(4-methylcyclohexyl)-3-triphenylmethoxy-1-iodo-1-trans-butene |
| 216 | 194 | 4-(3-methylcyclohexyl)-3-triphenylmethoxy-1-iodo-1-trans-butene |
| 217 | 195 | 3-(trans-2-methylcyclopentyl)-3-triphenylmethoxy-1-iodo-trans-propene |
| 218 | 196 | 3-cyclohexyl-3-triphenylmethoxy-1-iodo-1-trans-propene |
| 219 | 197 | 3-(trans-4-methylcyclohexyl)-3-triphenylmethoxy-1-iodo-1-trans-propene |
| 220 | 198 | 3-cyclooctyl-3-triphenylmethoxy-1-iodo-1-trans-propene |
| 221 | 199 | 3-cycloheptyl-3-triphenylmethoxy-1-iodo-1-trans-propene |

EXAMPLE 222

Preparation of 1-chloro-trans-1-octen-3-one

To a slurry of 233.5 g. (1.75 moles) of aluminum chloride in 390 ml. of carbon tetrachloride, saturated with acetylene and cooled in an ice bath, is added over 20 minutes 201.9 g. (150 moles) of hexanoyl chloride. After the addition is complete, acetylene is bubbled into the mixture is rapidly as it is absorbed and for 1 hour after absorption becomes slow. The mixture is poured onto 1700 g. of ice and 720 ml. of saturated brine. The organic phase is separated and the aqueous phase is washed with ether. The combined organic phase and washings are washed with saturated brine, dried ($Na_2SO_4$) and evaporated. The residual oil is combined with 10 g. of hydroquinone and distilled to yield a colorless oil, b.p. 51°–52° C. (0.10 torr.).

EXAMPLE 224

Preparation of 1-iodo-trans-1-octen-3-one

A mixture of 54.5 g. (0.364 mole) of sodium iodide and 40 g. (0.249 mole) of 1-chloro-trans-1-octen-3-one (Example 222) in 360 ml. of acetone is stirred and refluxed for 24 hours. The reaction mixture is cooled, filtered and concentrated. The residue is partitioned between water and ether. The organic phase is washed with dilute sodium bicarbonate solution, brine, dried ($MgSO_4$) and evaporated to an oil. This material is used directly without purification.

EXAMPLE 225

Preparation of 1-iodo-trans-1-octen-3-I

A solution of 78.2 g. (0.310 moles) of 1-iodo-trans-1-octene-3-one (Example 224) in 150 ml. of absolute ethanol is added dropwise over 2 hours to a slurry of 6.49 g. (0.172 moles) of sodium borohydride in 50 ml. of absolute ethanol cooled in an ice bath. After the addition is complete, the mixture is stirred for 2 hours with ice cooling and is then poured into 1 l. of water. The mixture is extracted into benzene and the organic phase is washed with saturated brine, dried ($Na_2SO_4$) and evaporated. The resulting oil id dissolved into 400 ml. of absolute ethanol and treated with 5 mole percent of p-carboxyphenylhydrazine at 70° C. for 1.5 hours to remove residual ketone. The mixture is cooled and evaporated and the residue is dissolved into 400 ml. of ether and is filtered. The filtrate is washed with dilute sodium bicarbonate solution and saturated brine, dried ($Na_2SO_4$), and evaporated to an oil. This oil is chromatographed upon 2 kg. of Florisil ® packed in hexane and the product is obtained upon elution with benzene. Distillation of the product yields a colorless oil, b.p. 74°–76° C. (0.005 torr.).

EXAMPLE 226

Preparation of 1-iodo-3-(p-anisyldiphenylmethoxy)-trans-1-octene

A mixture of 14.92 g. (0.0588 mole) of 1-iodo-trans-1-octen-3-ol (Example 225) and 18.2 g. (0.0588 mole) of p-anisyldiphenylmethyl chloride in 165 ml. of dry pyridine is heated at 60° C. for 18 hours under an inert atmosphere. The mixture is cooled and the solvent is evaporated in vacuo. The residue is partitioned between ether and water, and the organic phase is washed with water and saturated brine, dried ($MgSO_4$), and evaporated. The residue is chromatographed upon 300 g. of

EXAMPLE 227

Preparation of
9-oxo-11α-methoxy-15-hydroxy-13-trans-prostenoic acid

To a solution of 6.030 g. (0.01215 mole) of 1-iodo-3-triphenylmethoxy-trans-1-octene (Example 128) in 8 ml. of toluene cooled to −78° C. under an inert atmosphere is added 5.2 ml. of 2.34 M solution of n-butyllithium in hexane. The resulting solution is allowed to warm to −40° C. and is maintained at this temperature for 1 hour. To the solution containing 3-triphenylmethoxy-trans-1-octenyllithium is then added 5.0 ml. of a 2.44 M (0.0122 mole) solution of trimethylaluminum in heptane and the mixture is allowed to warm to −10° C. The mixture containing lithium trimethyl (3-triphenylmethoxy-trans-1-octenyl)alanate is then cooled to −78° C. and to it is added a solution of 3.94 g. (0.01215 mole) of 4-methoxy-2-(4-carbotetrahydropyran-2′-yloxyhexyl)-cyclopent-2-en-1-one (Example 101) dissolved in 10 ml. of diethyl ether. The mixture is allowed to warm to room temperature and is stirred at ambient temperature for 18 hours. The mixture is then poured onto ice and diluted hydrochloric acid and is extracted into ether. The organic phase is washed with water and saturated brine, dried (Na$_2$SO$_4$), and evaporated to yield a colorless oil.

The resulting crude 9-oxo-11α-methoxy-15-triphenylmethoxy-8$\xi$-13-trans-prostenoic acid is dissolved in 100 ml. of glacial acetic acid:tetrahydrofuran:water (4:2:1) and is heated at 45° C. for 7 hours. The mixture is cooled, diluted with aqueous sodium chloride solution and extracted with ether. The extract is washed with water and concentrated using toluene for azeotropic removal of aqueous acetic acid. The residue is chromatographed on silica gel to yield the title product and its 15-epimer.

EXAMPLES 228-393

Treatment of 1-iodo-3-triphenylmethoxy (or 3-methoxy)-trans-1-alkene listed in Table 12 below with n-butyl lithium followed by treatment of the resulting trans-1-alkenyl lithium derivative with trimethylaluminum and then treatment of the resulting lithio (trans-1-alkenyl) trimethyl alanate with the blocked 4-oxy-cyclopent-2-en 1-ones also listed in Table 12 below all by the procedure described in Example 227 gives, with the exception of the 15-methoxy derivative, the 15-O-triphenylmethyl-8-$\xi$-derivatives corresponding to the products of the table. Further treatment of these intermediates with acetic acid:tetrahydrofuran:water as described in Example 227 gives the products of the table.

TABLE 12

| Example | Starting 4-oxycyclopent-2-en-1-one of Example | Starting 1-iodo-1-trans alkene of Example | Product 9-oxo-11-oxy-15-hydroxy(methoxy)-13-trans-prostenoic acid |
|---|---|---|---|
| 228 | 101 | 143 | 9-oxo-11α-methoxy-15-hydroxy-20-ethyl-13-trans-prostenoic acid |
| 229 | 101 | 144 | 9-oxo-11α-methoxy-15-hydroxy-16-ethyl-13-trans-prostenoic acid |
| 230 | 101 | 148A | 9-oxo-11α-methoxy-15-methoxy-13-trans-prostenoic acid |
| 231 | 101 | 148 | 9-oxo-11α-methoxy-15-hydroxy-13-trans,17-cis-prostadienoic acid |
| 232 | 101 | 152 | 9-oxo-11α-methoxy-15-hydroxy-16,16-dimethyl-13-trans-prostenoic acid |
| 233 | 101 | 156 | 9-oxo-11α-methoxy-15-hydroxy-17,17-dimethyl-13-trans-prostenoic acid |
| 234 | 101 | 161 | 9-oxo-11α-methoxy-15-hydroxy-17,18-cis-methano-13-trans-prostenoic acid |
| 235 | 101 | 171 | 9-oxo-11α-methoxy-15-hydroxy-16,17,18,19,20-pentanor-15-(1-adamantyl)-trans-prostenoic acid |
| 236 | 101 | 172 | 9-oxo-11α-methoxy-15-hydroxy-16,20-methano-13-trans,17-prostadienoic acid |
| 237 | 101 | 221 | 9-oxo-11α-methoxy-15-hydroxy-16,20-ethano-13-trans-prostenoic acid |
| 238 | 101 | 219 | 9-oxo-11α-methoxy-15-hydroxy-16,19,-trans-ethano-13-trans-prostenoic acid |
| 239 | 87 | 140 | 9-oxo-11α-methoxy-15-hydroxy-6,7,19,20-tetranor-13-trans-prostenoic acid |
| 240 | 87 | 210 | 9-oxo-11α-methoxy-15-hydroxy-6,7-dinor-17,20-ethano-13-trans-prostenoic acid |
| 241 | 88 | 202 | 9-oxo-11α-ethoxy-15-hydroxy-5,6,7,20-tetranor-17-19-methano-13-trans-prostenoic acid |
| 242 | 88 | 141 | 9-oxo-11α-ethoxy-15-hydroxy-5,6,7,18,19,20-hexanor-13-trans-prostenoic acid |
| 243 | 89 | 143 | 9-oxo-11α-methoxy-15-hydroxy-7a,7b-bishomo-20-ethyl-13-trans-prostenoic acid |
| 244 | 89 | 152 | 9-oxo-11α-methoxy-15-hydroxy-7a,7b-bishomo-16,16-dimethyl-13-trans-prostenoic acid |
| 245 | 89 | 220 | 9-oxo-11α-methoxy-15-hydroxy-7a,7b-bishomo-16,20-(1,3-propano)-13-trans-prostenoic acid |
| 246 | 90 | 139 | 9-oxo-11α-methoxy-15-hydroxy-2-ethyl-20-nor-13-trans-prostenoic acid |
| 247 | 90 | 173 | 9-oxo-11α-methoxy-15-hydroxy-2-ethyl-16,20-methano-13-trans,18-prostadienoic acid |
| 248 | 91 | 175 | 9-oxo-11α-methoxy-15-hydroxy-3,3-dimethyl-16-(1-adamantyl)-17,18,19,20-tetranor-13-trans-prostenoic acid |
| 249 | 91 | 142 | 9-oxo-11α-methoxy-15-hydroxy-3,3,20-trimethyl-13- |

TABLE 12-continued

| Example | Starting 4-oxycyclopent-2-en-1-one of Example | Starting 1-iodo-1-trans alkene of Example | Product 9-oxo-11-oxy-15-hydroxy(methoxy)-13-trans-prostenoic acid |
|---|---|---|---|
| | | | trans-prostenoic acid |
| 250 | 92 | 128 | 9-oxo-11α-methoxy-15-hydroxy-3-oxa-13-trans-prostenoic acid |
| 251 | 92 | 148A | 9-oxo-11α,15-dimethoxy-3-oxa-13-trans-prostenoic acid |
| 252 | 92 | 152 | 9-oxo-11α-methoxy-15-hydroxy-3-oxa-16,16-dimethyl-13-trans-prostenoic acid |
| 253 | 92 | 169 | 9-oxo-11α-methoxy-15-hydroxy-3-oxa-17,20-ethano-13-trans,18-prostadienoic acid |
| 254 | 92 | 218 | 9-oxo-11α-methoxy-15-hydroxy-3-oxa-16,20-methano-13-trans-prostenoic acid |
| 255 | 93 | 203 | 9-oxo-11α-methoxy-15-hydroxy-2-fluoro-18,20-ethano-13-trans-prostenoic acid |
| 256 | 93 | 145 | 9-oxo-11α-methoxy-15-hydroxy-2-fluoro-16-methyl-20-nor-13-trans-prostenoic acid |
| 257 | 94 | 139 | 9-oxo-11α-methoxy-15-hydroxy-7,20-dinor-13-trans-prostenoic acid |
| 258 | 94 | 214 | 9-oxo-11α-methoxy-15-hydroxy-7-nor-17,20-(1,4-butano)-13-trans-prostenoic acid |
| 259 | 95 | 142 | 9-oxo-11α-methoxy-15-hydroxy-7a-homo-20-methyl-13-trans-prostenoic acid |
| 260 | 95 | 161 | 9-oxo-11α-methoxy-15-hydroxy-7a-homo-17,18-cis-methano-13-trans-prostenoic acid |
| 261 | 95 | 206 | 9-oxo-11α-methoxy-15-hydroxy-7a-homo-20-cyclopentyl-13-trans-prostenoic acid |
| 262 | 96 | 156 | 9-oxo-11α-methoxy-15-hydroxy-2-phenyl-17,17-dimethyl-13-trans-prostenoic acid |
| 263 | 96 | 211 | 9-oxo-11α-methoxy-15-hydroxy-2-phenyl-18,20-(1,3-propano)-13-trans-prostenoic acid |
| 264 | 97 | 152 | 9-oxo-11α-ethoxy-15-hydroxy-16,16-dimethyl-13-trans-prostenoic acid |
| 265 | 97 | 207 | 9-oxo-11α-ethoxy-15-hydroxy-16-methyl-18,20-ethano-13-trans-prostenoic acid |
| 266 | 97 | 146 | 9-oxo-11α-ethoxy-15-hydroxy-19-methyl-13-trans,18-prostadienoic acid |
| 267 | 97 | 148 | 9-oxo-11α-ethoxy-15-hydroxy-13-trans,17-cis-prostadienoic acid |
| 268 | 98 | 152 | 9-oxo-11α-propoxy-15-hydroxy-16,16-dimethyl-13-trans-prostenoic acid |
| 269 | 98 | 139 | 9-oxo-11α-propoxy-15-hydroxy-20-nor-13-trans-prostenoic acid |
| 270 | 98 | 128 | 9-oxo-11α-propoxy-15-hydroxy-13-trans-prostenoic acid |
| 271 | 98 | 174 | 9-oxo-11α-propoxy-15-hydroxy-16,17,18,19,20-pentanor-15-(2-adamantyl)-13-trans-prostenoic acid |
| 272 | 98 | 170 | 9-oxo-11α-propoxy-15-hydroxy-17,20-ethano-13-trans,19-prostadienoic acid |
| 273 | 99 | 148 | 9-oxo-11α-isopropoxy-15-hydroxy-13-trans,17-cis-prostadienoic acid |
| 274 | 99 | 148A | 9-oxo-11α-isopropoxy-15-methoxy-13-trans-prostenoic acid |
| 275 | 99 | 152 | 9-oxo-11α-isopropoxy-15-hydroxy-16,16-dimethyl-13-trans-prostenoic acid |
| 276 | 99 | 200 | 9-oxo-11α-isopropoxy-15-hydroxy-17,20-methano-13-trans-prostenoic acid |
| 277 | 99 | 226 | 9-oxo-11α-isopropoxy-15-hydroxy-13-trans-prostenoic acid |
| 278 | 100 | 152 | 9-oxo-4-n-butoxy-15-hydroxy-16,16-dimethyl-13-trans-prostenoic acid |
| 279 | 100 | 128 | 9-oxo-4-n-butoxy-15-hydroxy-13-trans-prostenoic acid |
| 280 | 100 | 145 | 9-oxo-4-n-butoxy-15-hydroxy-16-methyl-20-nor-13-trans-prostenoic acid |
| 281 | 100 | 208 | 9-oxo-4-n-butoxy-15-hydroxy-16-ethyl-19,20-(1,3-propano)-13-trans-prostenoic acid |
| 282 | 100 | 221 | 9-oxo-4-n-butoxy-15-hydroxy-16,20-ethano-13-trans-prostenoic acid |
| 283 | 102 | 217 | 9-oxo-11α-methoxy-15-hydroxy-2,17-dimethyl-20-nor-16,19-trans-methano-13-trans-prostenoic acid |
| 284 | 102 | 152 | 9-oxo-11α-methoxy-15-hydroxy-2,16,16-trimethyl-13-trans-prostenoic acid |
| 285 | 102 | 128 | 9-oxo-11α-methoxy-15-hydroxy-2-methyl-13-trans-prostenoic acid |
| 286 | 34 | 128 | ethyl 9-oxo-11α-ethoxy-15-hydroxy-13-trans-prostenoate |
| 287 | 34 | 215 | ethyl 9-oxo-11α-ethoxy-15-hydroxy-20-methyl-17,20-ethano-13-trans-prostenoate |
| 288 | 35 | 152 | methyl 9-oxo-11α-methoxy-15-hydroxy-16,16-dimethyl-13-trans-prostenoate |

TABLE 12-continued

| Example | Starting 4-oxycyclopent-2-en-1-one of Example | Starting 1-iodo-1-trans alkene of Example | Product 9-oxo-11-oxy-15-hydroxy(methoxy)-13-trans-prostenoic acid |
|---|---|---|---|
| 289 | 35 | 174 | methyl 9-oxo-11α-methoxy-15-hydroxy-16,17,18,19,-20-pentanor-15-(2-adamantyl)-13-trans-prostenoate |
| 290 | 36 | 226 | ethyl 9-oxo-11α-propoxy-15-hydroxy-6,7-dinor-13-trans-prostenoate |
| 291 | 37 | 128 | ethyl 9-oxo-11α-isopropoxy-15-hydroxy-5,6,7-trinor-13-trans-prostenoate |
| 292 | 41 | 147 | ethyl 9-oxo-11α-isopropoxy-15-hydroxy-7a,7b-bis-homo-17-methyl-20-(2-propenyl)-13-trans-prostenoate |
| 293 | 41 | 148 | ethyl 9-oxo-11α-isopropoxy-15-hydroxy-7a,7b-bis-homo-13-trans,17-prostadienoate |
| 294 | 43 | 148A | ethyl 9-oxo-11α-butoxy-15-methoxy-2-ethyl-13-trans-prostenoate |
| 295 | 43 | 152 | ethyl 9-oxo-11α-butoxy-15-hydroxy-2-ethyl-16,16-dimethyl-13-trans-prostenoate |
| 296 | 45 | 128 | ethyl 9-oxo-11α-methoxy-15-hydroxy-3,3-dimethyl-13-trans-prostenoate |
| 297 | 45 | 152 | ethyl 9-oxo-11α-methoxy-15-hydroxy-3,3,16,16-tetramethyl-13-trans-prostenoate |
| 298 | 47 | 143 | ethyl 9-oxo-11α-ethoxy-15-hydroxy-3-oxa-20-ethyl-13-trans-prostenoate |
| 299 | 47 | 204 | ethyl 9-oxo-11α-ethoxy-15-hydroxy-3-oxa-19,20-(1,3-propano)-13-trans-prostenoate |
| 300 | 50 | 142 | ethyl 9-oxo-11α-sec-butoxy-15-hydroxy-7-nor-20-methyl-13-trans-prostenoate |
| 301 | 50 | 212 | ethyl 9-oxo-11α-sec-butoxy-15-hydroxy-7-nor-19,20-(1,4-butano)-13-trans-prostenoate |
| 302 | 52 | 213 | ethyl 9-oxo-11α-methoxy-15-hydroxy-7α-homo-17,20-(1,3-propano)-13-trans-prostenoate |
| 303 | 52 | 148 | ethyl 9-oxo-11α-methoxy-15-hydroxy-7α-homo-13-trans,17-prostadienoate |
| 304 | 55 | 205 | butyl 9-oxo-11α-methoxy-15-hydroxy-20,20-(1,4-butano)-13-trans-prostenoate |
| 305 | 55 | 152 | butyl 9-oxo-11α-methoxy-15-hydroxy-16,16-dimethyl-13-trans-prostenoate |
| 306 | 55 | 128 | butyl 9-oxo-11α-methoxy-15-hydroxy-13-trans-prostenoate |
| 307 | 56 | 152 | isopropyl 9-oxo-11α-methoxy-15-hydroxy-16,16-dimethyl-13-trans-prostenoate |
| 308 | 56 | 128 | isopropyl 9-oxo-11α-methoxy-15-hydroxy-13-trans-prostenoate |
| 309 | 56 | 216 | isopropyl 9-oxo-11α-methoxy-15-hydroxy-17,19-(1,3-propano)-13-trans-prostenoate |
| 310 | 56 | 161 | isopropyl 9-oxo-11α-methoxy-15-hydroxy-17,18-cis-methano-13-trans-prostenoate |
| 311 | 57 | 128 | decyl 9-oxo-11α-methoxy-15-hydroxy-13-trans-prostenoate |
| 312 | 57 | 152 | decyl 9-oxo-11α-methoxy-15-hydroxy-16,16-dimethyl-13-trans-prostenoate |
| 313 | 57 | 143 | decyl 9-oxo-11α-methoxy-15-hydroxy-20-ethyl-13-trans-prostenoate |
| 314 | 57 | 213 | decyl 9-oxo-11α-methoxy-15-hydroxy-17,20-(1,3-propano)-13-trans-prostenoate |
| 315 | 57 | 201 | decyl 9-oxo-11α-methoxy-15-hydroxy-17,20-methano-13-trans-prostenoate |
| 316 | 62 | 128 | ethyl 9-oxo-11α-t-butoxy-15-hydroxy-13-trans-prostenoate |
| 317 | 62 | 152 | ethyl 9-oxo-11α-t-butoxy-15-hydroxy-16,16-dimethyl-13-trans-prostenoate |
| 318 | 62 | 209 | ethyl 9-oxo-11α-t-butoxy-15-hydroxy-20-nor-17,18-trans-(1,3-propano)-13-trans-prostenoate |
| 319 | 86 | 128 | 9-oxo-11α-(2-hydroxyethoxy)-15-hydroxy-13-trans-prostenoic acid |
| 320 | 86 | 152 | 9-oxo-11α-(2-hydroxyethoxy)-15-hydroxy-16,16-dimethyl-13-trans-prostenoic acid |
| 321 | 86 | 161 | 9-oxo-11α-(2-hydroxyethoxy)-15-hydroxy-17,18-cis-methano-13-trans-prostenoic acid |
| 322 | 86 | 171 | 9-oxo-11α-(2-hydroxyethoxy)-15-hydroxy-16,17,18,-19,20-pentanor-15-(1-adamantyl)-13-trans-prostenoic acid |
| 323 | 86 | 143 | 9-oxo-11α-(2-hydroxyethoxy)-15-hydroxy-20-ethyl-13-trans-prostenoic acid |
| 324 | 86 | 144 | 9-oxo-11α-(2-hydroxyethoxy)-15-hydroxy-16-ethyl-13-trans-prostenoic acid |
| 325 | 86 | 221 | 9-oxo-11α-(2-hydroxyethoxy)-15-hydroxy-16,20-ethano-13-trans-prostenoic acid |
| 326 | 86 | 148A | 9-oxo-11α-(2-hydroxyethoxy)-15-methoxy-13-trans-prostenoic acid |
| 327 | 86 | 148 | 9-oxo-11α-(2-hydroxyethoxy)-15-hydroxy-13-trans,- |

TABLE 12-continued

| Example | Starting 4-oxycyclopent-2-en-1-one of Example | Starting 1-iodo-1-trans alkene of Example | Product 9-oxo-11-oxy-15-hydroxy(methoxy)-13-trans-prostenoic acid |
|---|---|---|---|
| | | | 17-cis-prostadienoic acid |
| 328 | 107 | 140 | 9-oxo-11α-(2-hydroxyethoxy)-15-hydroxy-6,7,19,20-tetranor-13-trans-prostenoic acid |
| 329 | 107 | 210 | 9-oxo-11α-(2-hydroxyethoxy)-15-hydroxy-6,7-dinor-17,20-ethano-13-trans-prostenoic acid |
| 330 | 108 | 141 | 9-oxo-11α-(2-hydroxyethoxy)-15-hydroxy-5,6,7,18,-19,20-hexanor-13-trans-prostenoic acid |
| 331 | 108 | 221 | 9-oxo-11α-(2-hydroxyethoxy)-15-hydroxy-5,6,7-trinor-16,20-ethano-13-trans-prostenoic acid |
| 332 | 110 | 143 | 9-oxo-11α-(2-hydroxyethoxy)-15-hydroxy-7a,7b-bishomo-20-ethyl-13-trans-prostenoic acid |
| 333 | 110 | 152 | 9-oxo-11α-(2-hydroxyethoxy)-15-hydroxy-7a,7b-bishomo-16,16-dimethyl-13-trans-prostenoic acid |
| 334 | 110 | 128 | 9-oxo-11α-(2-hydroxyethoxy)-15-hydroxy-7a,7b-bishomo-13-trans-prostenoic acid |
| 335 | 110 | 220 | 9-oxo-11α-(2-hydroxyethoxy)-15-hydroxy-7a,7b-bishomo-16,20-(1,3-propano)-13-trans-prostenoic acid |
| 336 | 111 | 206 | 9-oxo-11α-(2-hydroxyethoxy)-15-hydroxy-2-ethyl-20-cyclopentyl-13-trans-prostenoic acid |
| 337 | 111 | 148 | 9-oxo-11α-(2-hydroxyethoxy)-15-hydroxy-2-ethyl-13-trans,17-cis-prostadienoic acid |
| 338 | 113 | 128 | 9-oxo-11α-(2-hydroxyethoxy)-15-hydroxy-3,3-dimethyl-13-trans-prostenoic acid |
| 339 | 113 | 144 | 9-oxo-11α-(2-hydroxyethoxy)-15-hydroxy-3,3-dimethyl-16-ethyl-13-trans-prostenoic acid |
| 340 | 113 | 213 | 9-oxo-11α-(2-hydroxyethoxy)-15-hydroxy-3,3-dimethyl-17,20-(1,3-propano)-13-trans-prostenoic acid |
| 341 | 115 | 128 | 9-oxo-11α-(2-hydroxyethoxy)-15-hydroxy-3-oxa-13-trans-prostenoic acid |
| 342 | 115 | 152 | 9-oxo-11α-(2-hydroxyethoxy)-15-hydroxy-3-oxa-16,-16-dimethyl-13-trans-prostenoic acid |
| 343 | 115 | 219 | 9-oxo-11α-(2-hydroxyethoxy)-15-hydroxy-3-oxa-16,-19-trans-ethano-13-trans-prostenoic acid |
| 344 | 115 | 148A | 9-oxo-11α-(2-hydroxyethoxy)-15-methoxy-3-oxa-13-trans-prostenoic acid |
| 345 | 115 | 148 | 9-oxo-11α-(2-hydroxyethoxy)-15-hydroxy-3-oxa-13-trans,17-prostadienoic acid |
| 346 | 115 | 172 | 9-oxo-11α-(2-hydroxyethoxy)-15-hydroxy-3-oxa-16,-20-methano-13-trans,17-cis-prostadienoic acid |
| 347 | 117 | 152 | 9-oxo-11α-(2-hydroxyethoxy)-15-hydroxy-2-fluoro-16,16-dimethyl-13-trans-prostenoic acid |
| 348 | 117 | 128 | 9-oxo-11α-(2-hydroxyethoxy)-15-hydroxy-2-fluoro-13-trans-prostenoic acid |
| 349 | 117 | 214 | 9-oxo-11α-(2-hydroxyethoxy)-15-hydroxy-2-fluoro-17,20-(1,4-butano)-13-trans prostenoic acid |
| 350 | 118 | 139 | 9-oxo-11α-(2-hydroxyethoxy)-15-hydroxy-7,20-bisnor-13-trans-prostenoic acid |
| 351 | 118 | 145 | 9-oxo-11α-(2-hydroxyethoxy)-15-hydroxy-7,20-bisnor-16-methyl-13-trans-prostenoic acid |
| 352 | 119 | 142 | 9-oxo-11α-(2-hydroxyethoxy)-15-hydroxy-7a-homo-20-methyl-13-trans prostenoic acid |
| 353 | 119 | 152 | 9-oxo-11α-(2-hydroxyethoxy)-15-hydroxy-7a-homo-16,16-dimethyl-13-trans prostenoic acid |
| 354 | 119 | 174 | 9-oxo-11α-(2-hydroxyethoxy)-15-hydroxy-7a-homo-16,17,18,19,20-pentanor-15-(2-adamantyl)-13-trans-prostenoic acid |
| 355 | 120 | 128 | 9-oxo-11α-(2-hydroxyethoxy)-15-hydroxy-2-phenyl-13-trans-prostenoic acid |
| 356 | 124 | 128 | 9-oxo-11α-(2-hydroxypropoxy)-15-hydroxy-13-trans-prostenoic acid |
| 357 | 124 | 152 | 9-oxo-11α-(2-hydroxypropoxy)-15-hydroxy-16,16-dimethyl-13-trans-prostenoic acid |
| 358 | 124 | 207 | 9-oxo-11α-(2-hydroxypropoxy)-15-hydroxy-16-methyl-18,20-ethano-13-trans prostenoic acid |
| 359 | 124 | 148 | 9-oxo-11α-(2-hydroxypropoxy)-15-hydroxy-13-trans-17-cis-prostadienoic acid |
| 360 | 126 | 128 | 9-oxo-11α-(4-hydroxybutoxy)-15-hydroxy-13-trans-prostenoic acid |
| 361 | 126 | 152 | 9-oxo-11α-(4-hydroxybutoxy)-15-hydroxy-16,16-dimethyl-13-trans prostenoic acid |
| 362 | 103 | 152 | ethyl 9-oxo-11α-(2-hydroxyethoxy)-15-hydroxy-16,-16-dimethyl-13-trans-prostenoate |
| 363 | 103 | 147 | ethyl 9-oxo-11α-(2-hydroxyethoxy)-15-hydroxy-17-methyl-20-(2-propenyl)-13-trans-prostenoate |
| 364 | 103 | 217 | ethyl 9-oxo-11α-(2-hydroxyethoxy)-15-hydroxy-19,-20-dinor-16,17-(1,3-propano)-13-trans-prostenoate |
| 365 | 103 | 212 | ethyl 9-oxo-11α-(2-hydroxyethoxy)-15-hydroxy-19,-20-(1,4-butano)-13-trans-prostenoate |
| 366 | 104 | 139 | methyl 9-oxo-11α-(2-hydroxyethoxy)-15-hydroxy-20- |

TABLE 12-continued

| Example | Starting 4-oxycyclopent-2-en-1-one of Example | Starting 1-iodo-1-trans alkene of Example | Product 9-oxo-11-oxy-15-hydroxy(methoxy)-13-trans-prostenoic acid |
|---|---|---|---|
| | | | nor-13-trans-prostenoate |
| 367 | 104 | 148A | methyl 9-oxo-11α-(2-hydroxyethoxy)-15-methoxy-13-trans-prostenoate |
| 368 | 105 | 202 | ethyl 9-oxo-11α-(2-hydroxypropoxy)-15-hydroxy-6,7,20-trinor-17,19-methano-13-trans-prostenoate |
| 369 | 106 | 208 | ethyl 9-oxo-11α-(2-hydroxyethoxy)-15-hydroxy-5,6,7-trinor-16-ethyl-19,20-(1,3-propano)-13-trans-prostenoate |
| 370 | 109 | 161 | ethyl 9-oxo-11α-(2-hydroxyethoxy)-15-hydroxy-7a,7b-bishomo-17,18-cis-methano-13-trans-prostenoate |
| 371 | 109 | 148 | ethyl 9-oxo-11α-(2-hydroxyethoxy)-15-hydroxy-7a,7b-bishomo-13-trans,17-cis-prostadienoate |
| 372 | 109 | 169 | ethyl 9-oxo-11α-(2-hydroxyethoxy)-15-hydroxy-7a,7b-bishomo-17,20-ethano-13-trans,18-prostadienoate |
| 373 | 112 | 148 | ethyl 9-oxo-11α-(3-hydroxypropoxy)-15-hydroxy-2-ethyl-13-trans,17-cis-prostadienoate |
| 374 | 112 | 203 | ethyl 9-oxo-11α-(3-hydroxypropoxy)-15-hydroxy-2-ethyl-18,20-ethano-13-trans-prostenoate |
| 375 | 114 | 156 | ethyl 9-oxo-11α-(2-hydroxyethoxy)-15-hydroxy-3,3,17,17-tetramethyl-13-trans-prostenoate |
| 376 | 114 | 215 | ethyl 9-oxo-11α-(2-hydroxyethoxy)-15-hydroxy-3,3,20-trimethyl-17,20-ethano-13-trans-prostenoate |
| 377 | 116 | 152 | ethyl 9-oxo-11α-(3-hydroxypropoxy)-15-hydroxy-3-oxa-16,16-dimethyl-13-trans-prostenoate |
| 378 | 116 | 218 | ethyl 9-oxo-11α-(3-hydroxypropoxy)-15-hydroxy-3-oxa-16,20-methano-13-trans-prostenoate |
| 379 | 121 | 128 | butyl 9-oxo-11α-(2-hydroxyethoxy)-15-hydroxy-13-trans-prostenoate |
| 380 | 121 | 152 | butyl 9-oxo-11α-(2-hydroxyethoxy)-15-hydroxy-16,16-dimethyl-13-trans-prostenoate |
| 381 | 121 | 161 | butyl 9-oxo-11α-(2-hydroxyethoxy)-15-hydroxy-17,18-cis-methano-13-trans prostenoate |
| 382 | 121 | 216 | butyl 9-oxo-11α-(2-hydroxyethoxy)-15-hydroxy-17,19-(1,3-propano)-13-trans-prostenoate |
| 383 | 121 | 173 | butyl 9-oxo-11α-(2-hydroxyethoxy)-15-hydroxy-16,20-methano-13-trans,18-prostadienoate |
| 384 | 121 | 148 | butyl 9-oxo-11α-(2-hydroxyethoxy)-15-hydroxy-13-trans,17-cis-prostadienoate |
| 385 | 122 | 148 | isopropyl 9-oxo-11α-(2-hydroxyethoxy)-15-hydroxy-13-trans,17-cis-prostadienoate |
| 386 | 122 | 146 | isopropyl 9-oxo-11α-(2-hydroxyethoxy)-15-hydroxy-19-methyl-13-trans,18-prostadienoate |
| 387 | 122 | 152 | isopropyl 9-oxo-11α-(2-hydroxyethoxy)-15-hydroxy-16,16-dimethyl-13-trans-prostenoate |
| 388 | 122 | 175 | isopropyl 9-oxo-11α-(2-hydroxyethoxy)-15-hydroxy-17,18,19,20-tetranor-16-(1-adamantyl)-13-trans-prostenoate |
| 389 | 123 | 128 | decyl 9-oxo-11α-(2-hydroxyethoxy)-15-hydroxy-13-trans-prostenoate |
| 390 | 123 | 152 | decyl 9-oxo-11α-(2-hydroxyethoxy)-15-hydroxy-16,16-dimethyl-13-trans-prostenoate |
| 391 | 123 | 148A | decyl 9-oxo-11α-(2-hydroxyethoxy)-15-methoxy-13-trans-prostenoate |
| 392 | 123 | 209 | decyl 9-oxo-11α-(2-hydroxyethoxy)-15-hydroxy-20-nor-17,18-trans-)1,3-propano)-13-trans-prostenoate |
| 393 | 123 | 148 | decyl 9-oxo-11α-(2-hydroxyethoxy)-15-hydroxy-13-trans,17-cis-prostadienoate |

EXAMPLE 394

Preparation of 9α,15-dihydroxy-11α-methoxy-13-trans-prostenoic acid

To a solution of 433 mg. of 9-oxo-11α-methoxy-15-hydroxy-13-trans-prostenoic acid (Example 227) in 4.5 ml. of tetrahydrofuran, stirred in an ice bath under nitrogen atmosphere, is added dropwise 3.7 ml. of 0.76M lithium perhydro-9b-boraphenyalyl hydride. After 40 minutes at 0° C. there is added 1.62 ml. of 3N sodium hydroxide followed by 1.62 ml. of 30% hydrogen peroxide. Ether is added and the resulting solution is acidified with 2N hydrochloric acid. The ether layer is washed several times with saturated sodium chloride solution, dried with anhydrous magnesium sulfate and taken to dryness to give the subject product as an oil.

EXAMPLES 395–560

Treatment of the 9-oxo derivatives listed in Table 13 below the lithium perhydro-9b-boraphenyalyl hydride by the procedure described above in Example 394 furnishes the product 9α-hydroxy-11-oxy-15-hydroxy(or methoxy)-13-trans-prostenoic acids of the table.

TABLE 13

| Example | Starting 9-oxo derivative of Example | Product 9α-hydroxy-11-oxy-15-hydroxy(methoxy)-13-trans-prostenoic acid |
|---|---|---|
| 395 | 228 | 9α-hydroxy-11α-methoxy-15-hydroxy-20-ethyl-13-trans-prostenoic acid |
| 396 | 229 | 9α-hydroxy-11α-methoxy-15-hydroxy-16-ethyl-13-trans-prostenoic acid |
| 397 | 230 | 9α-hydroxy-11α-methoxy-15-methoxy-13-trans-prostenoic acid |
| 398 | 231 | 9α-hydroxy-11α-methoxy-15-hydroxy-13-trans,17-cis-prostadienoic acid |
| 399 | 232 | 9α-hydroxy-11α-methoxy-15-hydroxy-16,16-dimethyl-13-trans-prostenoic acid |
| 400 | 233 | 9α-hydroxy-11α-methoxy-15-hydroxy-17,17-dimethyl-13-trans-prostenoic acid |
| 401 | 234 | 9α-hydroxy-11α-methoxy-15-hydroxy-17,18-cis-methano-13-trans-prostenoic acid |
| 402 | 235 | 9α-hydroxy-11α-methoxy-15-hydroxy-16,17,18,19,20-pentanor-15-(1-adamantyl)-13-trans-prostenoic acid |
| 403 | 236 | 9α-hydroxy-11α-methoxy-15-hydroxy-16,20-methano-13-trans,17-prostadienoic acid |
| 404 | 237 | 9α,15-dihydroxy-11α-methoxy-16,20-ethano-13-trans-prostenoic acid |
| 405 | 238 | 9α-hydroxy-11α-methoxy-15-hydroxy-16,19-trans-ethano-13-trans-prostenoic acid |
| 406 | 239 | 9α-hydroxy-11α-methoxy-15-hydroxy-6,7,19,20-tetranor-13-trans-prostenoic acid |
| 407 | 240 | 9α-hydroxy-11α-methoxy-15-hydroxy-6,7-dinor-17,20-ethano-13-trans-prostenoic acid |
| 408 | 241 | 9α-hydroxy-11α-ethoxy-15-hydroxy-5,6,7,20-tetranor-17,19-methano-13-trans-prostenoic acid |
| 409 | 242 | 9α-hydroxy-11α-ethoxy-15-hydroxy-5,6,7,18,19,20-hexanor-13-trans-prostenoic acid |
| 410 | 243 | 9α-hydroxy-11α-methoxy-15-hydroxy-7a,7b-bishomo-20-ethyl-13-trans-prostenoic acid |
| 411 | 244 | 9α-hydroxy-11α-methoxy-15-hydroxy-7a,7b-bishomo-16,16-dimethyl-13-trans-prostenoic acid |
| 412 | 245 | 9α-hydroxy-11α-methoxy-15-hydroxy-7a,7b-bishomo-16,20(1,3-propano)-13-trans-prostenoic acid |
| 413 | 246 | 9α-hydroxy-11α-methoxy-15-hydroxy-2-ethyl-20-nor-13-trans-prostenoic acid |
| 414 | 247 | 9α-hydroxy-11α-methoxy-15-hydroxy-2-ethyl-16,20-methano-13-trans,18-prostadienoic acid |
| 415 | 248 | 9α-hydroxy-11α-methoxy-3,3-dimethyl-16-(1-adamantyl)-17,18,19,20-tetranor-13-trans-prostenoic acid |
| 416 | 249 | 9α-hydroxy-11α-methoxy-15-hydroxy-3,3,20-trimethyl-13-trans-prostenoic acid |
| 417 | 250 | 9α-hydroxy-11α-methoxy-15-hydroxy-3-oxa-13-trans-prostenoic acid |
| 418 | 251 | 9α-hydroxy-11α,15-dimethoxy-3-oxa-13-trans-prostenoic acid |
| 419 | 252 | 9α-hydroxy-11α-methoxy-15-hydroxy-3-oxa-16,16-dimethyl-13-trans-prostenoic acid |
| 420 | 253 | 9α-hydroxy-11α-methoxy-15-hydroxy-3-oxa-17,20-ethano-13-trans-18-prostadienoic acid |
| 421 | 254 | 9α-hydroxy-11α-methoxy-15-hydroxy-3-oxa-16,20-methano-13-trans-prostenoic acid |
| 422 | 255 | 9α-hydroxy-11α-methoxy-15-hydroxy-2-fluoro-18,20-ethano-13-trans-prostenoic acid |
| 423 | 256 | 9α-hydroxy-11α-methoxy-15-hydroxy-2-fluoro-16-methyl-20-nor-13-trans-prostenoic acid |
| 424 | 257 | 9α-hydroxy-11α-methoxy-15-hydroxy-7,20-dinor-13-trans-prostenoic acid |
| 425 | 258 | 9α-hydroxy-11α-methoxy-15-hydroxy-7-nor-17,20-(1,4-butano)-13-trans-prostenoic acid |
| 426 | 259 | 9α-hydroxy-11α-methoxy-15-hydroxy-7a-homo-20-methyl-13-trans-prostenoic acid |
| 427 | 260 | 9α-hydroxy-11α-methoxy-15-hydroxy-7a-homo-17,18-cis-methano-13-trans-prostenoic acid |
| 428 | 261 | 9α-hydroxy-11α-methoxy-15-hydroxy-7a-homo-20-cyclopentyl-13-trans-prostenoic acid |
| 429 | 262 | 9α-hydroxy-11α-methoxy-15-hydroxy-2-phenyl-17,17-dimethyl-13-trans-prostenoic acid |
| 430 | 263 | 9α-hydroxy-11α-methoxy-15-hydroxy-2-phenyl-18,20-(1,3-propano)-13-trans-prostenoic acid |
| 431 | 264 | 9α-hydroxy-11α-ethoxy-15-hydroxy-16,16-dimethyl-13-trans-prostenoic acid |
| 432 | 265 | 9α-hydroxy-11α-ethoxy-15-hydroxy-16-methyl-18,20-ethano-13-trans-prostenoic acid |
| 433 | 266 | 9α-hydroxy-11α-ethoxy-15-hydroxy-19-methyl- |

TABLE 13-continued

| Example | Starting 9-oxo derivative of Example | Product 9α-hydroxy-11-oxy-15-hydroxy(methoxy)-13-trans-prostenoic acid |
|---|---|---|
| | | 13-trans,18-prostadienoic acid |
| 434 | 267 | 9α-hydroxy-11α-ethoxy-15-hydroxy-13-trans-17-prostadienoic acid |
| 435 | 268 | 9α-hydroxy-11α-propoxy-16,16-dimethyl-13-trans-prostenoic acid |
| 436 | 269 | 9α-hydroxy-11α-propoxy-15-hydroxy-20-nor-13-trans-prostenoic acid |
| 437 | 270 | 9α-hydroxy-11α-propoxy-15-hydroxy-13-trans-prostenoic acid |
| 438 | 271 | 9α-hydroxy-11α-propoxy-16,17,18,19,20-pentanor-15-(2-adamantyl)-13-trans-prostenoic acid |
| 439 | 272 | 9α-hydroxy-11α-propoxy-15-hydroxy-17,20-ethano-13-trans,19-prostadienoic acid |
| 440 | 273 | 9α-hydroxy-11α-isopropoxy-15-hydroxy-13-trans,17-prostadienoic acid |
| 441 | 274 | 9α-hydroxy-11α-isopropoxy-15-methoxy-13-trans-prostenoic acid |
| 442 | 275 | 9α-hydroxy-11α-isopropoxy-15-hydroxy-16,16-dimethyl-13-trans-prostenoic acid |
| 443 | 276 | 9α-hydroxy-11α-isopropoxy-15-hydroxy-17,20-methano-13-trans-prostenoic acid |
| 444 | 277 | 9α-hydroxy-11α-isopropoxy-15-hydroxy-13-trans-prostenoic acid |
| 445 | 278 | 9α-hydroxy-4-n-butoxy-15-hydroxy-16,16-dimethyl-13-trans-prostenoic acid |
| 446 | 279 | 9α-hydroxy-4-n-butoxy-15-hydroxy-13-trans-prostenoic acid |
| 447 | 280 | 9α-hydroxy-4-n-butoxy-16-methyl-20-nor-13-trans-prostenoic acid |
| 448 | 281 | 9α-hydroxy-4-n-butoxy-16-ethyl-19,20-(1,3-propano)-13-trans-prostenoic acid |
| 449 | 282 | 9α-hydroxy-4-n-butoxy-15-hydroxy-16,20-ethano-13-trans-prostenoic acid |
| 450 | 283 | 9α-hydroxy-11α-methoxy-15-hydroxy-2,17-dimethyl-20-nor-16,19-trans-methano-13-trans-prostenoic acid |
| 451 | 284 | 9α-hydroxy-11α-methoxy-15-hydroxy-2,16,16-trimethyl-13-trans-prostenoic acid |
| 452 | 285 | 9α-hydroxy-11α-methoxy-15-hydroxy-2-methyl-13-trans-prostenoic acid |
| 453 | 286 | ethyl 9α-hydroxy-11α-ethoxy-15-hydroxy-13-trans-prostenoate |
| 454 | 287 | ethyl 9α-hydroxy-11α-ethoxy-15-hydroxy-20-methyl-17,20-ethano-13-trans-prostenoate |
| 455 | 288 | methyl 9α-hydroxy-11α-methoxy-15-hydroxy-16,16-dimethyl-13-trans-prostenoate |
| 456 | 289 | methyl 9α-hydroxy-11α-methoxy-15-hydroxy-16,17,18,19,20-pentanor-15-(2-adamantyl)-13-trans-prostenoate |
| 457 | 290 | ethyl 9α-hydroxy-11α-propoxy-15-hydroxy-6,7-dinor-13-trans-prostenoate |
| 458 | 291 | ethyl 9α-hydroxy-11α-isopropoxy-15-hydroxy-5,6,7-trinor-13-trans-prostenoate |
| 459 | 292 | ethyl 9α-hydroxy-11α-isopropoxy-15-hydroxy-7a,7b-bishomo-17-methyl-20-(2-propenyl)-13-trans-prostenoate |
| 460 | 293 | ethyl 9α-hydroxy-11α-isopropoxy-15-hydroxy-7a,7b-bishomo-13-trans,17-prostadienoate |
| 461 | 294 | ethyl 9α-hydroxy-11α-butoxy-15-methoxy-2-ethyl-13-trans-prostenoate |
| 462 | 295 | ethyl 9α-hydroxy-11α-butoxy-15-hydroxy-2-ethyl-16,16-dimethyl-13-trans-prostenoate |
| 463 | 296 | ethyl 9α-hydroxy-11α-methoxy-15-hydroxy-3,3-dimethyl-13-trans-prostenoate |
| 464 | 297 | ethyl 9α-hydroxy-11α-methoxy-15-hydroxy-3,3,16,16-tetramethyl-13-trans-prostenoate |
| 465 | 298 | ethyl 9α-hydroxy-11α-ethoxy-15-hydroxy-3-oxa-20-ethyl-13-trans-prostenoate |
| 466 | 299 | ethyl 9α-hydroxy-11α-ethoxy-15-hydroxy-3-oxa-19,20-(1,3-propano)-13-trans-prostenoate |
| 467 | 300 | ethyl 9α-hydroxy-11α-sec-butoxy-15-hydroxy-7-nor-20-methyl-13-trans-prostenoate |
| 468 | 301 | ethyl 9α-hydroxy-11α-sec-butoxy-15-hydroxy-7-nor-19,20-(1,4-butano)-13-trans-prostenoate |
| 469 | 302 | ethyl 9α-hydroxy-11α-methoxy-15-hydroxy-7a-homo-17,20-(1,3-propano)-13-trans-prostenoate |
| 470 | 303 | ethyl 9α-hydroxy-11α-methoxy-15-hydroxy-7a-homo-13-trans-17-prostadienoate |
| 471 | 304 | butyl 9α-hydroxy-11α-methoxy-15-hydroxy-20,20-(1,4-butano)-13-trans-prostenoate |

TABLE 13-continued

| Example | Starting 9-oxo derivative of Example | Product 9α-hydroxy-11-oxy-15-hydroxy(methoxy)-13-trans-prostenoic acid |
|---|---|---|
| 472 | 305 | butyl 9α-hydroxy-11α-methoxy-15-hydroxy-16,16-dimethyl-13-trans-prostenoate |
| 473 | 306 | butyl 9α-hydroxy-11α-methoxy-15-hydroxy-13-trans-prostenoate |
| 474 | 307 | isopropyl 9α-hydroxy-11α-methoxy-15-hydroxy-16,16-dimethyl-13-trans-prostenoate |
| 475 | 308 | isopropyl 9α-hydroxy-11α-methoxy-15-hydroxy-13-trans-prostenoate |
| 476 | 309 | isopropyl 9α-hydroxy-11α-methoxy-15-hydroxy-17,19-(1,3-propano)-13-trans-prostenoate |
| 477 | 310 | isopropyl 9α-hydroxy-11α-methoxy-15-hydroxy-17,18-cis-methano-13-trans-prostenoate |
| 478 | 311 | decyl 9α-hydroxy-11α-methoxy-15-hydroxy-13-trans-prostenoate |
| 479 | 312 | decyl 9α-hydroxy-11α-methoxy-15-hydroxy-16,16-dimethyl-13-trans-prostenoate |
| 480 | 313 | decyl 9α-hydroxy-11α-methoxy-15-hydroxy-20-ethyl-13-trans-prostenoate |
| 481 | 314 | decyl 9α-hydroxy-11α-methoxy-15-hydroxy-17,20-(1,3-propano)-13-trans-prostenoate |
| 482 | 315 | decyl 9α-hydroxy-11α-methoxy-15-hydroxy-17,20-methano-13-trans-prostenoate |
| 483 | 316 | ethyl 9α-hydroxy-11α-t-butoxy-15-hydroxy-13-trans-prostenoate |
| 484 | 317 | ethyl 9α-hydroxy-11α-t-butoxy-15-hydroxy-16,16-dimethyl-13-trans-prostenoate |
| 485 | 318 | ethyl 9α-hydroxy-11α-t-butoxy-20-nor-17,18-trans-1,3-propano-13-trans-prostenoate |
| 486 | 319 | 9α-hydroxy-11α-(2-hydroxyethoxy)-15-hydroxy-13-trans-prostenoic acid |
| 487 | 320 | 9α-hydroxy-11α-(2-hydroxyethoxy)-15-hydroxy-16,16-dimethyl-13-trans-prostenoic acid |
| 488 | 321 | 9α-hydroxy-11α-(2-hydroxyethoxy)-15-hydroxy-17,18-cis-methano-13-trans-prostenoic acid |
| 489 | 322 | 9α-hydroxy-11α-(2-hydroxyethoxy)-15-hydroxy-16,17,18,19,20-pentanor-15-(1-adamantyl)-13-trans-prostenoic acid |
| 490 | 323 | 9α-hydroxy-11α-(2-hydroxyethoxy)-15-hydroxy-20-ethyl-13-trans-prostenoic acid |
| 491 | 324 | 9α-hydroxy-11α-(2-hydroxyethoxy)-15-hydroxy-16-ethyl-13-trans-prostenoic acid |
| 492 | 325 | 9α-hydroxy-11α-(2-hydroxyethoxy)-15-hydroxy-16,20-ethano-13-trans-prostenoic acid |
| 493 | 326 | 9α-hydroxy-11α-(2-hydroxyethoxy)-15-methoxy-13-trans-prostenoic acid |
| 494 | 327 | 9α-hydroxy-11α-(2-hydroxyethoxy)-15-hydroxy-13-trans,17-cis prostadienoic acid |
| 495 | 328 | 9α-hydroxy-11α-(2-hydroxyethoxy)-15-hydroxy-6,7,19,20-tetranor-13-trans-prostenoic acid |
| 496 | 329 | 9α-hydroxy-11α-(2-hydroxyethoxy)-6,7-dinor-17,20-ethano-13-trans-prostenoic acid |
| 497 | 330 | 9α-hydroxy-11α-(2-hydroxyethoxy)-15-hydroxy-5,6,7,18,19,20-hexanor-13-trans-prostenoic acid |
| 498 | 331 | 9α-hydroxy-11α-(2-hydroxyethoxy)-15-hydroxy-5,6,7-trinor-16,20-ethano-13-trans-prostenoic acid |
| 499 | 332 | 9α-hydroxy-11α-(2-hydroxyethoxy)-15-hydroxy-7a,7b-bishomo-20-ethyl-13-trans-prostenoic acid |
| 500 | 333 | 9α-hydroxy-11α-(2-hydroxyethoxy)-15-hydroxy-7a,7b-bishomo-16,16-dimethyl-13-trans-prostenoic acid |
| 501 | 334 | 9α-hydroxy-11α-(2-hydroxyethoxy)-15-hydroxy-7a,7b-bishomo-13-trans-prostenoic acid |
| 502 | 335 | 9α-hydroxy-11α-(2-hydroxyethoxy)-15-hydroxy-7a,7b-bishomo-16,20-(1,3-propano)-13-trans-prostenoic acid |
| 503 | 336 | 9α-hydroxy-11α-(2-hydroxyethoxy)-15-hydroxy-2-ethyl-20-cyclopentyl-13-trans-prostenoic acid |
| 504 | 337 | 9α-hydroxy-11α-(2-hydroxyethoxy)-15-hydroxy-2-ethyl-13-trans,17-cis-prostadienoic acid |
| 505 | 338 | 9α-hydroxy-11α-(2-hydroxyethoxy)-15-hydroxy-3,3-dimethyl-13-trans-prostenoic acid |
| 506 | 339 | 9α-hydroxy-11α-(2-hydroxyethoxy)-15-hydroxy-3,3-dimethyl-16-ethyl-13-trans-prostenoic acid |
| 507 | 340 | 9α-hydroxy-11α-(2-hydroxyethoxy)-15-hydroxy-3,3-dimethyl-17,20-(1,3-propano)-13- |

TABLE 13-continued

| Example | Starting 9-oxo derivative of Example | Product 9α-hydroxy-11-oxy-15-hydroxy(methoxy)-13-trans-prostenoic acid |
|---|---|---|
| 508 | 341 | trans-prostenoic acid 9α-hydroxy-11α-(2-hydroxyethoxy)-15-hydroxy-3-oxa-13-trans-prostenoic acid |
| 509 | 342 | 9α-hydroxy-11α-(2-hydroxyethoxy)-15-hydroxy-3-oxa-16,16-dimethyl-13-trans-prostenoic acid |
| 510 | 343 | 9α-hydroxy-11α-(2-hydroxyethoxy)-15-hydroxy-3-oxa-16,19-trans-ethano-13-trans-prostenoic acid |
| 511 | 344 | 9α-hydroxy-11α-(2-hydroxyethoxy)-15-methoxy-3-oxa-13-trans-prostenoic acid |
| 512 | 345 | 9α-hydroxy-11α-(2-hydroxyethoxy)-15-hydroxy-3-oxa-13-trans,17-cis-prostadienoic acid |
| 513 | 346 | 9α-hydroxy-11α-(2-hydroxyethoxy)-15-hydroxy-3-oxa-16,20-methano-13-trans,17-prostadienoic acid |
| 514 | 347 | 9α-hydroxy-11α-(2-hydroxyethoxy)-15-hydroxy-2-fluoro-16,16-dimethyl-13-trans-prostenoic acid |
| 515 | 348 | 9α-hydroxy-11α-(2-hydroxyethoxy)-15-hydroxy-2-fluoro-13-trans-prostenoic acid |
| 516 | 349 | 9α-hydroxy-11α-(2-hydroxyethoxy)-15-hydroxy-2-fluoro-17,20-(1,4-butano-13-trans-prostenoic acid |
| 517 | 350 | 9α-hydroxy-11α-(2-hydroxyethoxy)-15-hydroxy-7,20-bisnor-13-trans-prostenoic acid |
| 518 | 351 | 9α-hydroxy-11α-(2-hydroxyethoxy)-15-hydroxy-7,20-bisnor-16-methyl-13-trans-prostenoic acid |
| 519 | 352 | 9α-hydroxy-11α-(2-hydroxyethoxy)-15-hydroxy-7a-homo-20-methyl-13-trans-prostenoic acid |
| 520 | 353 | 9α-hydroxy-11α-(2-hydroxyethoxy)-15-hydroxy-7a-homo-16,16-dimethyl-13-trans-prostenoic acid |
| 521 | 354 | 9α-hydroxy-11α-(2-hydroxyethoxy)-15-hydroxy-7a-homo-16,17,18,19,20-pentanor-15-(2-adamantyl)-13-trans-prostenoic acid |
| 522 | 355 | 9α-hydroxy-11α-(2-hydroxyethoxy)-15-hydroxy-2-phenyl-13-trans-prostenoic acid |
| 523 | 356 | 9α-hydroxy-11α-(2-hydroxypropoxy)-15-hydroxy-13-trans-prostenoic acid |
| 524 | 357 | 9α-hydroxy-11α-(2-hydroxypropoxy)-15-hydroxy-16,16-dimethyl-13-trans-prostenoic acid |
| 525 | 358 | 9α-hydroxy-11α-(2-hydroxypropoxy)-15-hydroxy-16-methyl-18,20-ethano-13-trans-prostenoic acid |
| 526 | 359 | 9α-hydroxy-11α-(2-hydroxypropoxy)-15-hydroxy-13-trans,17-cis-prostadienoic acid |
| 527 | 360 | 9α-hydroxy-11α-(4-hydroxybutoxy)-15-hydroxy-13-trans-prostenoic acid |
| 528 | 361 | 9α-hydroxy-11α-(4-hydroxybutoxy)-15-hydroxy-16,16-dimethyl-13-trans-prostenoic acid |
| 529 | 362 | ethyl 9α-hydroxy-11α-(2-hydroxyethoxy)-15-hydroxy-16,16-dimethyl-13-trans-prostenoate |
| 530 | 363 | ethyl 9α-hydroxy-11α-(2-hydroxyethoxy)-15-hydroxy-17-methyl-20-(2-propenyl)-13-trans-prostenoate |
| 531 | 364 | ethyl 9α-hydroxy-11α-(2-hydroxyethoxy)-15-hydroxy-19,20-dinor-16,17-(1,3-propano)-13-trans-prostenoate |
| 532 | 365 | ethyl 9α-hydroxy-11α-(2-hydroxyethoxy)-15-hydroxy-19,20-(1,4-butano)-13-trans-prostenoate |
| 533 | 366 | methyl 9α-hydroxy-11α-(2-hydroxyethoxy)-15-hydroxy-20-nor-13-trans-prostenoate |
| 534 | 367 | methyl 9α-hydroxy-11α-(2-hydroxyethoxy)-15-methoxy-13-trans-prostenoate |
| 535 | 368 | ethyl 9α-hydroxy-11α-(3-hydroxypropoxy)-15-hydroxy-6,7,20-trinor-17,19-methano-13-trans-prostenoate |
| 536 | 369 | ethyl 9α-hydroxy-11α-(2-hydroxyethoxy)-15-hydroxy-5,6,7-trinor-16-ethyl-19,20-(1,3-propano-13-trans-prostenoate |
| 537 | 370 | ethyl 9α-hydroxy-11α-(2-hydroxyethoxy)-15-hydroxy-7a,7b-bishomo-17,18-cis-methano-13-trans-prostenoate |
| 538 | 371 | ethyl 9α-hydroxy-11α-(2-hydroxyethoxy)-15-hydroxy-7a,7b-bishomo-13-trans,17-cis-prostadienoate |
| 539 | 372 | ethyl 9α-hydroxy-11α-(2-hydroxyethoxy)-15-hydroxy-7a,7b-bishomo-17,20-ethano-13-trans-18-prostadienoate |
| 540 | 373 | ethyl 9α-hydroxy-11α-(3-hydroxypropoxy)-15-hydroxy-2-ethyl-13-trans,17-cis-prostadienoate |
| 541 | 374 | ethyl 9α-hydroxy-11α- |

TABLE 13-continued

| Example | Starting 9-oxo derivative of Example | Product 9α-hydroxy-11-oxy-15-hydroxy(methoxy)-13-trans-prostenoic acid |
|---|---|---|
| | | (3-hydroxypropoxy)-15-hydroxy-2-ethyl-18,20-ethano-13-trans-prostenoate |
| 542 | 375 | ethyl 9α-hydroxy-11α-(3-hydroxyethoxy)-3,3,17,17-tetramethyl-13-trans-prostenoate |
| 543 | 376 | ethyl 9α-hydroxy-11α-(2-hydroxyethoxy)-15-hydroxy-3,3,20-trimethyl-17,20-ethano-13-trans-prostenoate |
| 544 | 377 | ethyl 9α-hydroxy-11α-(3-hydroxypropoxy)-15-hydroxy-3-oxa-16,16-dimethyl-13-trans-prostenoate |
| 545 | 378 | ethyl 9α-hydroxy-11α-(3-hydroxypropoxy)-15-hydroxy-3-oxa-16,20-methano-13-trans-prostenoate |
| 546 | 379 | butyl 9α-hydroxy-11α-(2-hydroxyethoxy)-15-hydroxy-13-trans-prostenoate |
| 547 | 380 | butyl 9α-hydroxy-11α-(2-hydroxyethoxy)-15-hydroxy-16,16-dimethyl-13-trans-prostenoate |
| 548 | 381 | butyl 9α-hydroxy-11α-(2-hydroxyethoxy)-15-hydroxy-17,18-cis-methano-13-trans-prostenoate |
| 549 | 382 | butyl 9α-hydroxy-11α-(2-hydroxyethoxy-15-hydroxy-17,19-(1,3-propano-13-trans-prostenoate |
| 550 | 383 | butyl 9α-hydroxy-11α-(2-hydroxyethoxy)-15-hydroxy-16,20-methano-13-trans,18-prostadienoate |
| 551 | 384 | butyl 9α-hydroxy-11α-(2-hydroxyethoxy)-15-hydroxy-13-trans,17-cis-prostenoate |
| 552 | 385 | isopropyl 9α-hydroxy-11α-(2-hydroxyethoxy)-15-hydroxy-13-trans,-17-cis-prostadienoate |
| 553 | 386 | isopropyl-9α-hydroxy-11α-(2-hydroxyethoxy)-15-hydroxy-19-methyl-13-trans,18-prostadienoate |
| 554 | 387 | isopropyl 9α-hydroxy-11α-(2-hydroxyethoxy)-15-hydroxy-16,16-dimethyl-13-trans-prostenoate |
| 555 | 388 | isopropyl 9α-hydroxy-11α-(2-hydroxyethoxy)-15-hydroxy-17,18,19,-20-tetranor-16-(1-adamantyl)-13-trans-prostenoate |
| 556 | 389 | decyl 9α-hydroxy-11α-(2-hydroxyethoxy)-15-hydroxy-13-trans-prostenoate |
| 557 | 390 | decyl 9α-hydroxy-11α-(2-hydroxyethoxy)-15-hydroxy-16,16-dimethyl-13-trans-prostenoate |
| 558 | 391 | decyl 9α-hydroxy-11α-(2-hydroxyethoxy)-15-methoxy-13-trans-prostenoate |
| 559 | 392 | decyl 9α-hydroxy-11α-(2-hydroxyethoxy)-15-hydroxy-20-nor-17,18-trans(1,3-propano)-13-trans-prostenoate |
| 560 | 393 | decyl 9α-hydroxy-11α-(2-hydroxyethoxy)-15-hydroxy-13-trans,17-cis-prostadienoate |

EXAMPLE 561

A solution of 9-oxo-11α-methoxy-15-hydroxy-13-trans-prostenoic acid (Example 227) in tetrahydrofuran is added to 2.2 equivalents of lithium perhydro-9b-boraphenyalyl hydride in tetrahydrofuran at −78° C. After 30 minutes the solution is diluted with water and extracted with ether. The aqueous phase is acidified, saturated with sodium chloride and extracted with ether. The combined ether extracts are dried (magnesium sulfate) and concentrated in vacuo to give 9α,15α-dihydroxy-11α-methoxy-13-trans-prostenoic acid, contaminated with 9β,15α-dihydroxy-11α-methoxy-13-trans prostenoic acid. The crude mixture of acids is dissolved in methylene chloride and added to a refluxing solution of 1.2 equivalents of 2,3-dichloro-5,6-dicyanobenzoquinone (DDQ) in methylene chloride. After 5 hours, the solution is cooled and filtered. The filtrate is concentrated in vacuo and the residue is purified by column chromatography to give 9α-hydroxy-11α-methoxy-15-oxo-13-trans-prostenoic acid. This material is dissolved in benzene and 2.2 equivalents each of trimethylsilyl chloride and triethylamine; triethylamine hydrochloride is removed by filtration and the solution is concentrated in vacuo to give trimethylsilyl 9α-trimethylsiloxy-11α-methoxy-15-oxo13-trans-prostenoate.

The siloxy derivative is dissolved in ether at 0° C. and 1.05 equivalents of methyl magnesium bromide in ether is added. After the reaction is complete, the solution is poured into saturated aqueous ammonium chloride and extracted with ether. The ether is dried and concentrated in vacuo to give an oil. The oil is dissolved in methanol:water:acetic acid (approximately 10:1:1). After three hours at ambient temperatures, the solution is diluted with water, saturated with sodium chloride and extracted with ether. The ether extracts are dried and concentrated in vacuo to give 9α,15α-dihydroxy-15β-methyl-11α-methoxy-13-trans-prostenoic acid and 9α,15β-dihydroxy-15α-methyl-11α-methoxy-13-trans-prostenoic acid, which are separated by dry column chromatography.

Treatment of a solution of 9α,15α-dihydroxy-15β-methyl-11α-methoxy-13-trans-prostenoic acid with chromic acid-pyridine in methylene chloride (Collins Reagent) followed by addition to dilute acid and extraction with ether gives 9-oxo-11α-methoxy-15α-hydroxy-15β-methyl-13-trans-prostenoic acid.

Similar treatment of the corresponding 15β-hydroxy acid gives 9-oxo11α-methoxy-15β-hydroxy-15α-methyl-prostenoic acid.

EXAMPLES 562–605

Treatment of the 9-oxo-15-hydroxy prostenoic acids of Table 14 below by the sequence of reactions described in Example 561 is productive of the 9-oxo-15-hydroxy-15-methyl products of the table. Also prepared in the course of these reaction sequences are the 9α-hydroxy derivative corresponding to the products of the table and the 15-keto derivatives of the 9α- and 9β-hydroxy compounds corresponding to the 9-oxo starting compounds, and the 9α- or 9β-trimethylsilyloxy trimethylsilyl esters of the 15-keto and 15-hydroxy-15-methyl compounds. In the instances of the 11α-(ω-hydroxyalkoxy)derivatives silylation is carried out with 3.3 equivalents each of trimethylsilyl chloride and triethylamine in order to provide silylation of the ω-hydroxy group. In all cases both the 15α-hydroxy-15β-methyl and the 15β-hydroxy-15α-methyl products and intermediates are obtained. The epimers are separable by chromatographic procedures.

TABLE 14

| Example | Starting 9-oxo-11-oxy-15-hydroxy prostenoic acid of Example | Product 9-oxo-11-oxy-15-hydroxy-15-methyl-13-trans-prostenoic acid |
|---|---|---|
| 562 | 228 | 9-oxo-11α-methoxy-15-hydroxy-15-methyl-20-ethyl-13-trans-prostenoic acid |
| 563 | 231 | 9-oxo-11α-methoxy-15-hydroxy-15-methyl-13-trans, 17-cis-prostadienoic acid |
| 564 | 239 | 9-oxo-11α-methoxy-15-hydroxy-15-methyl-6,7,19,20-tetranor-13-trans-prostenoic acid |
| 565 | 242 | 9-oxo-11α-ethoxy-15-hydroxy-15-methyl-5,6,7,18,19 20-hexanor-13-trans-prostenoic acid |
| 566 | 243 | 9-oxo-11α-methoxy-15-hydroxy-15-methyl-7a,7b-bishomo-20-ethyl-13-trans-prostenoic acid |
| 567 | 246 | 9-oxo-11α-methoxy-15-hydroxy-15-methyl-2-ethyl-20-nor-13-trans-prostenoic acid |
| 568 | 249 | 9-oxo-11α-methoxy-15-hydroxy-15-methyl-3,3,20-trimethyl-13-trans-prostenoic acid |
| 569 | 250 | 9-oxo-11α-methoxy-15-hydroxy-15-methyl-3-oxa-13-trans-prostenoic acid |
| 570 | 253 | 9-oxo-11α-methoxy-15-hydroxy-15-methyl-3-oxa-17,20-ethano-13-trans,18-prostadienoic acid |
| 571 | 255 | 9-oxo-11α-methoxy-15-hydroxy-15-methyl-2-fluoro-18,20-ethano-13-trans-prostenoic acid |
| 572 | 257 | 9-oxo-11α-methoxy-15-hydroxy-15-methyl-7,20-dinor-13-trans-prostenoic acid |
| 573 | 258 | 9-oxo-11α-methoxy-15-hydroxy-15-methyl-7-nor-17,20-(1,4-butano)-13-trans-prostenoic acid |
| 574 | 259 | 9-oxo-11α-methoxy-15-hydroxy-15-methyl-7a-homo-20-methyl-13-trans-prostenoic acid |
| 575 | 260 | 9-oxo-11α-methoxy-15-hydroxy-15-methyl-7a-homo-17,18-cis-methano-13-trans-prostenoic acid |
| 576 | 261 | 9-oxo-11α-methoxy-15-hydroxy-15-methyl-20-cyclopentyl-7a-homo-13-trans-prostenoic acid |
| 577 | 263 | 9-oxo-11α-methoxy-15-hydroxy-15-methyl-2-phenyl-18,20-(1,3-propano)-13-trans-prostenoic acid |
| 578 | 266 | 9-oxo-11α-ethoxy-15-hydroxy-15-methyl-19-methyl-13-trans,18-prostadienoic acid |
| 579 | 267 | 9-oxoα-ethoxy-15-hydroxy-15-methyl-13-trans,17-cis-prostadienoic acid |
| 580 | 269 | 9-oxo-11α-propoxy-15-hydroxy-15-methyl-20-nor-13-trans-prostenoic acid |
| 581 | 270 | 9-oxo-11α-propoxy-15-hydroxy-15-methyl-13-trans-prostenoic acid |
| 582 | 273 | 9-oxo-11α-isopropoxy-15-hydroxy-15-methyl-13-trans-17-cis-prostadienoic acid |
| 583 | 277 | 9-oxo-11α-isopropoxy-15-hydroxy-15-methyl-13-trans-prostenoic acid |
| 584 | 279 | 9-oxo-4-n-butoxy-15-hydroxy-15-methyl-13-trans-prostenoic acid |
| 585 | 285 | 9-oxo-11α-methoxy-15-hydroxy-15-methyl-2-methyl-13-trans-prostenoic acid |
| 586 | 319 | 9-oxo-11α-(2-hydroxyethoxy)-15-hydroxy-15-methyl-13-trans-prostenoic acid |
| 587 | 321 | 9-oxo-11α-(2-hydroxyethoxy)-15-hydroxy-15-methyl-17,18-cis-methano-13-trans-prostenoic acid |
| 588 | 323 | 9-oxo-11α-(2-hydroxyethoxy)-15-hydroxy-15-methyl-20-ethyl-13-trans-prostenoic acid |
| 589 | 327 | 9-oxo-11α-(2-hydroxyethoxy)-15-hydroxy-15-methyl-13-trans,17-cis-prostadienoic acid |
| 590 | 328 | 9-oxo-11α-(2-hydroxyethoxy)-15-hydroxy-15-methyl-6,7,19,20-tetranor-13-trans-prostenoic acid |
| 591 | 330 | 9-oxo-11α-(2-hydroxyethoxy)-15-hydroxy-15-methyl-5,6,7,18,19,20-hexanor-13-trans-prostenoic acid |
| 592 | 332 | 9-oxo-11α-(2-hydroxyethoxy)-15-hydroxy-15-methyl-7a,7b-bishomo-20-ethyl-13-trans- |

TABLE 14-continued

| Example | Starting 9-oxo-11-oxy-15-hydroxy prostenoic acid of Example | Product 9-oxo-11-oxy-15-hydroxy-15-methyl-13-trans-prostenoic acid |
|---|---|---|
| 593 | 334 | 9-oxo-11α-(2-hydroxyethoxy)-15-hydroxy-15-methyl-7a,7b-bishomo-13-trans-prostenoic acid |
| 594 | 336 | 9-oxo-11α-(2-hydroxyethoxy)-15-hydroxy-15-methyl-2-ethyl-20-cyclopentyl-13-trans-prostenoic acid |
| 595 | 337 | 9-oxo-11α-(2-hydroxyethoxy)-15-hydroxy-15-methyl-2-ethyl-13-trans,17-cis-prostadienoic acid |
| 596 | 338 | 9-oxo-11α-(2-hydroxyethoxy)-15-hydroxy-15-methyl-3,3-dimethyl-13-trans-prostenoic acid |
| 597 | 341 | 9-oxo-11α-(2-hydroxyethoxy)-15-hydroxy-15-methyl-3-oxa-13-trans-prostenoic acid |
| 598 | 345 | 9-oxo-11α-(2-hydroxyethoxy)-15-hydroxy-15-methyl-3-oxa-13-trans,17-cis-prostadienoic acid |
| 599 | 348 | 9-oxo-11α-(2-hydroxyethoxy)-15-hydroxy-15-methyl-2-fluoro-13-trans-prostenoic acid |
| 600 | 350 | 9-oxo-11α-(2-hydroxyethoxy)-15-hydroxy-15-methyl-7,20-bisnor-13-trans-prostenoic acid |
| 601 | 352 | 9-oxo-11α-(2-hydroxyethoxy)-15-hydroxy-15-methyl-7α-homo-20-methyl-13-trans-prostenoic acid |
| 602 | 355 | 9-oxo-11α-(2-hydroxyethoxy)-15-hydroxy-15-methyl-2-phenyl-13-trans-prostenoic acid |
| 603 | 356 | 9-oxo-11α-(2-hydroxypropoxy)-15-hydroxy-15-methyl-13-trans-prostenoic acid |
| 604 | 359 | 9-oxo-11α-(2-hydroxypropoxy)-15-hydroxy-15-methyl-13-trans,17-cis-prostadienoic acid |
| 605 | 360 | 9-oxo-11α-(4-hydroxybutoxy)-15-hydroxy-15-methyl-13-trans-prostenoic acid |

EXAMPLE 606

Preparation of
9-oxo-11α-methoxy-15-hydroxy-prostanoic acid

A 2 g. sample of 9-oxo-11α-methoxy-15-hydroxy-13-trans-prostenoic acid (Example 227) is hydrogenated using 700 mg. of 10% palladium on carbon in 50 ml. of absolute alcohol. The catalyst is removed in filtration and the mother liquor is taken to dryness to give 2 g. of subject compound as an oil.

EXAMPLE 607

Not included: 608 follows directly after 606.

EXAMPLES 608–835

Catalytic hydrogenation of the 13-trans-prostenoic acids and esters listed in Table 15 below by the procedure described in Example 606 furnishes the product prostanoic acids and esters of the table.

TABLE 15

| Example | Starting 13-trans-prostenoic acid or ester of Example | Product 11-oxy-15-oxy-prostanoic acid or ester |
|---|---|---|
| 608 | 228 | 9-oxo-11α-methoxy-15-hydroxy-20-ethyl-prostanoic acid |
| 609 | 229 | 9-oxo-11α-methoxy-15-hydroxy-16-ethyl-prostanoic acid |
| 610 | 230 | 9-oxo-11α-methoxy-15-methoxy-prostanoic acid |
| 611 | 232 | 9-oxo-11α-methoxy-15-hydroxy-16,16-dimethyl-prostanoic acid |
| 612 | 233 | 9-oxo-11α-methoxy-15-hydroxy-17,17-dimethyl-prostanoic acid |
| 613 | 234 | 9-oxo-11α-methoxy-15-hydroxy-17,18-cis-methano-prostanoic acid |
| 614 | 235 | 9-oxo-11α-methoxy-15-hydroxy-16,17,18,19,20-pentano)-15-(1-adamantyl)-prostanoic acid |
| 615 | 237 | 9-oxo-11α-methoxy-15-hydroxy-16,20-ethano-prostanoic acid |
| 616 | 238 | 9-oxo-11α-methoxy-15-hydroxy-16,19-trans-ethano-prostanoic acid |
| 617 | 239 | 9-oxo-11α-methoxy-15-hydroxy-6,7,19,20-tetranor-prostanoic acid |
| 618 | 242 | 9-oxo-11α-methoxy-15-hydroxy-5,6,7,18,19,20-hexanor-prostanoic acid |
| 619 | 243 | 9-oxo-11α-methoxy-15-hydroxy-7a,7b-bishomo-20-ethyl-prostanoic acid |
| 620 | 244 | 9-oxo-11α-methoxy-15-hydroxy-7a,7b-bishomo-16,16-dimethyl-prostanoic acid |
| 621 | 245 | 9-oxo-11α-methoxy-15-hydroxy-7a,7b-bishomo-16,20-(1,3-propano)-prostanoic acid |
| 622 | 246 | 9-oxo-11α-methoxy-15-hydroxy-2-ethyl-20-nor-prostanoic acid |
| 623 | 248 | 9-oxo-11α-methoxy-15-hydroxy-3,3-dimethyl-16(1-adamantyl)-17,18,19,20-tetranor-prostanoic acid |
| 624 | 250 | 9-oxo-11α-methoxy-15-hydroxy-3-oxa-prostanoic acid |
| 625 | 251 | 9-oxo-11α,15-dimethoxy-3-oxa-prostanoic acid |
| 626 | 252 | 9-oxo-11α-methoxy-15-hydroxy-3-oxa-16,16-dimethyl-prostanoic acid |
| 627 | 254 | 9-oxo-11α-methoxy-15-hydroxy-17,20-ethano-prostanoic acid |
| 628 | 255 | 9-oxo-11α-methoxy-15-hydroxy-2-fluoro-18,20-ethano-prostanoic acid |
| 629 | 257 | 9-oxo-11α-methoxy-15-hydroxy-7,20-dinor- |

TABLE 15-continued

| Example | Starting 13-trans-prostenoic acid or ester of Example | Product 11-oxy-15-oxy-prostanoic acid or ester |
|---|---|---|
| 630 | 259 | 9-oxo-11α-methoxy-15-hydroxy-7a-homo-20-methyl-prostanoic acid |
| 631 | 260 | 9-oxo-11α-methoxy-15-hydroxy-7a-homo-17,18-cis-methano-prostanoic acid |
| 632 | 262 | 9-oxo-11α-methoxy-15-hydroxy-2-phenyl-17,17-dimethyl-prostanoic acid |
| 633 | 264 | 9-oxo-11α-ethoxy-15-hydroxy-16,16-dimethyl-prostanoic acid |
| 634 | 268 | 9-oxo-11α-propoxy-15-hydroxy-16,16-dimethyl-prostanoic acid |
| 635 | 270 | 9-oxo-11α-propoxy-15-hydroxy-prostanoic acid |
| 636 | 271 | 9-oxo-11α-propoxy-15-hydroxy-16,17,18,19,20-pentanor-15-(2-adamantyl)-prostanoic acid |
| 637 | 274 | 9-oxo-11α-isopropoxy-15-methoxy-prostanoic acid |
| 638 | 275 | 9-oxo-11α-isopropoxy-15-hydroxy-16,16-dimethyl-prostanoic acid |
| 639 | 277 | 9-oxo-11α-isopropoxy-prostanoic acid |
| 640 | 278 | 9-oxo-4-n-butoxy-15-hydroxy-16,16-dimethyl-prostanoic acid |
| 641 | 279 | 9-oxo-4-n-butoxy-15-hydroxy-prostanoic acid |
| 642 | 282 | 9-oxo-4-n-butoxy-15-hydroxy-16,20-ethano-prostanoic acid |
| 643 | 284 | 9-oxo-11α-methoxy-15-hydroxy-2,16,16-trimethyl-prostanoic acid |
| 644 | 285 | 9-oxo-11α-methoxy-15-hydroxy-2-methyl-prostanoic acid |
| 645 | 286 | ethyl 9-oxo-11α-ethoxy-15-hydroxy-prostanoate |
| 646 | 288 | methyl 9-oxo-11α-methoxy-15-hydroxy-16,16-dimethyl-prostanoate |
| 647 | 295 | ethyl 9-oxo-11α-butoxy-15-hydroxy-2-ethyl-16,16-dimethyl-prostanoate |
| 648 | 296 | ethyl 9-oxo-11α-methoxy-15-hydroxy-3,3-dimethyl-prostanoate |
| 649 | 297 | ethyl 9-oxo-11α-methoxy-15-hydroxy-3,3,16,16-tetramethyl-prostanoate |
| 650 | 298 | ethyl 9-oxo-11α-ethoxy-15-hydroxy-3-oxa-20-ethyl-prostanoate |
| 651 | 300 | ethyl 9-oxo-11α-sec-butoxy-15-hydroxy-7-nor-20-methyl-prostanoate |
| 652 | 302 | ethyl 9-oxo-11α-methoxy-15-hydroxy-7a-homo-17,20-(1,3-propano)prostanoate |
| 653 | 304 | butyl 9-oxo-11α-methoxy-15-hydroxy-20,20-(1,4-butano)-prostanoate |
| 654 | 305 | butyl 9-oxo-11α-methoxy-15-hydroxy-16,16-dimethyl-prostanoate |
| 655 | 306 | butyl 9-oxo-11α-methoxy-15-hydroxy-prostanoate |
| 656 | 307 | isopropyl 9-oxo-11α-methoxy-15-hydroxy-16,16-dimethyl-prostanoate |
| 657 | 308 | isopropyl 9-oxo-11α-methoxy-15-hydroxy-prostanoate |
| 658 | 310 | isopropyl 9-oxo-11α-methoxy-15-hydroxy-17,18-cis-methano-prostanoate |
| 659 | 311 | decyl 9-oxo-11α-methoxy-15-hydroxy-prostanoate |
| 660 | 312 | decyl 9-oxo-11α-methoxy-15-hydroxy-16,16-dimethyl-prostanoate |
| 661 | 314 | decyl 9-oxo-11α-methoxy-15-hydroxy-17,20-(1,3-propano)-prostanoate |
| 662 | 316 | ethyl 9-oxo-11α-t-butoxy-15-hydroxy-prostanoate |
| 663 | 317 | ethyl 9-oxo-11α-t-butoxy-15-hydroxy-16,16-dimethyl-prostanoate |
| 664 | 319 | 9-oxo-11α-(2-hydroxyethoxy)-15-hydroxy-prostanoic acid |
| 665 | 320 | 9-oxo-11α-(2-hydroxyethoxy)-15-hydroxy-16,16-dimethyl-prostanoic acid |
| 666 | 321 | 9-oxo-11α-(2-hydroxyethoxy)-15-hydroxy-17,18-cis-methano-prostanoic acid |
| 667 | 322 | 9-oxo-11α-(2-hydroxyethoxy)-15-hydroxy-16,17,18,19,20-pentanor-15-(1-adamantyl)-prostanoic acid |
| 668 | 323 | 9-oxo-11α-(2-hydroxyethoxy)-15-hydroxy-20-ethyl-prostanoic acid |
| 669 | 325 | 9-oxo-11α-(2-hydroxyethoxy)-15-hydroxy-16,20-ethano-prostanoic acid |
| 670 | 326 | 9-oxo-11α-(2-hydroxyethoxy)-15-methoxy-prostanoic acid |
| 671 | 328 | 9-oxo-11α-(2-hydroxyethoxy)-15-hydroxy-6,7,19,20-tetranor-prostanoic acid |
| 672 | 330 | 9-oxo-11α-(2-hydroxyethoxy)-15-hydroxy-5,6,7,18,19,20-hexanor-prostanoic acid |
| 673 | 332 | 9-oxo-11α-(2-hydroxyethoxy)-15-hydroxy-7a,7b-bishomo-20-ethyl-prostanoic acid |
| 674 | 333 | 9-oxo-11α-(2-hydroxyethoxy)-15-hydroxy-7a,7b-bishomo-16,16-dimethyl-prostanoic acid |
| 675 | 334 | 9-oxo-11α-(2-hydroxyethoxy)-15-hydroxy-7a,7b-bishomo-prostanoic acid |
| 676 | 335 | 9-oxo-11α-(2-hydroxyethoxy)-15-hydroxy-7a,7b-bishomo-16,20-(1,3-propano)-prostanoic acid |
| 677 | 336 | 9-oxo-11α-(2-hydroxyeth- |

TABLE 15-continued

| Example | Starting 13-trans-prostenoic acid or ester of Example | Product 11-oxy-15-oxy-prostanoic acid or ester |
|---|---|---|
| | | oxy)-15-hydroxy-2-ethyl-20-cyclopentyl-prostanoic acid |
| 678 | 338 | 9-oxo-11α-(2-hydroxyethoxy)-15-hydroxy-3,3-dimethyl-prostanoic acid |
| 679 | 341 | 9-oxo-11α-(2-hydroxyethoxy)-15-hydroxy-3-oxa-prostanoic acid |
| 680 | 342 | 9-oxo-11α-(2-hydroxyethoxy)-15-hydroxy-3-oxa-16,16-dimethyl-prostanoic acid |
| 681 | 343 | 9-oxo-11α-(2-hydroxyethoxy)-15-hydroxy-3-oxa-16,19-trans-ethano-prostanoic acid |
| 682 | 344 | 9-oxo-11α-(2-hydroxyethoxy)-15-methoxy-3-oxa-prostanoic acid |
| 683 | 347 | 9-oxo-11α-(2-hydroxyethoxy)-15-hydroxy-2-fluoro-16,16-dimethyl-prostanoic acid |
| 684 | 350 | 9-oxo-11α-(2-hydroxyethoxy)-15-hydroxy-7,20-bisnor-prostanoic acid |
| 685 | 352 | 9-oxo-11α-(2-hydroxyethoxy)-15-hydroxy-7a-homo-20-methyl-prostanoic acid |
| 686 | 353 | 9-oxo-11α-(2-hydroxyethoxy)-15-hydroxy-7a-homo-16,16-dimethyl-prostanoic acid |
| 687 | 355 | 9-oxo-11α-(2-hydroxyethoxy)-15-hydroxy-2-phenyl-prostanoic acid |
| 688 | 356 | 9-oxo-11α-(2-hydroxypropoxy)-15-hydroxy-prostanoic acid |
| 689 | 357 | 9-oxo-11α-(2-hydroxypropoxy)-15-hydroxy-16,16-dimethyl-prostanoic acid |
| 690 | 360 | 9-oxo-11α-(4-hydroxybutoxy)-15-hydroxy-prostanoic acid |
| 691 | 361 | 9-oxo-11α-(4-hydroxybutoxy)-15-hydroxy-16,16-dimethyl-prostanoic acid |
| 692 | 362 | ethyl 9-oxo-11α-(2-hydroxyethoxy)-15-hydroxy 16,16-dimethyl-prostanoate |
| 693 | 366 | methyl 9-oxo-11α-(2-hydroxyethoxy)-15-hydroxy-20-nor-prostanoate |
| 694 | 367 | methyl 9-oxo-11α-(2-hydroxyethoxy)-15-methoxy-prostanoate |
| 695 | 370 | ethyl 9-oxo-11α-(2-hydroxyethoxy)-15-hydroxy-7a,7b-bishomo-17,18-cis-methano-prostanoate |
| 696 | 377 | ethyl 9-oxo-11α-(2-hydroxypropoxy)-15-hydroxy-3-oxa-16,16-dimethyl-prostanoate |
| 697 | 379 | butyl 9-oxo-11α-(2-hydroxyethoxy)-15-hydroxy-prostanoate |
| 698 | 380 | butyl 9-oxo-11α-(2-hydroxyethoxy)-15-hydroxy-16,16-dimethyl-prostanoate |
| 699 | 381 | butyl 9-oxo-11α-(2-hydroxyethoxy)-15-hydroxy-17,18-cis-methano-prostanoate |
| 700 | 387 | isopropyl 9-oxo-11α-(2-hydroxyethoxy)-15-hydroxy-16,16-dimethyl-prostanoate |
| 701 | 389 | decyl 9-oxo-11α-(2-hydroxyethoxy)-15-hydroxy-prostanoate |
| 702 | 390 | decyl 9-oxo-11α-(2-hydroxyethoxy)-15-hydroxy-16,16-dimethyl-prostanoate |
| 703 | 391 | decyl 9-oxo-11α-(2-hydroxyethoxy)-15-methoxy-prostanoate |
| 704 | 392 | decyl 9-oxo-11α-(2-hydroxyethoxy)15-hydroxy-20-nor-17,18-trans-(1,3-propano)-prostanoate |
| 705 | 395 | 9α-hydroxy-11α-methoxy-15-hydroxy-20-ethyl-prostanoic acid |
| 706 | 396 | 9α-hydroxy-11α-methoxy-15-hydroxy-16-ethyl-prostanoic acid |
| 707 | 397 | 9α-hydroxy-11α-methoxy-15-methoxy-prostanoic acid |
| 708 | 399 | 9α-hydroxy-11α-methoxy-15-hydroxy-16,16-dimethyl-prostanoic acid |
| 709 | 401 | 9α-hydroxy-11α-methoxy-15-hydroxy-17,18-cis-methano-prostanoic acid |
| 710 | 402 | 9α-hydroxy-11α-methoxy-15-hydroxy-16,17,18,19,20-pentanor-15-(1-adamantyl)-prostanoic acid |
| 711 | 404 | 9α-hydroxy-11α-methoxy-15-hydroxy-16,20-ethano-prostanoic acid |
| 712 | 405 | 9α-hydroxy-11α-methoxy-15-hydroxy-16,19-trans-ethano-prostanoic acid |
| 713 | 406 | 9α-hydroxy-11α-methoxy-15-hydroxy-6,7,19,20-tetranor-prostanoic acid |
| 714 | 410 | 9α-hydroxy-11α-methoxy-15-hydroxy-7a,7b-bishomo-20-ethyl-prostanoic acid |
| 715 | 411 | 9α-hydroxy-11α-methoxy-15-hydroxy-7a,7b-bishomo-16,16-dimethyl-prostanoic acid |
| 716 | 413 | 9α-hydroxy-11α-methoxy-15-hydroxy-2-ethyl-20-nor-prostanoic acid |
| 717 | 416 | 9α-hydroxy-11α-methoxy-15-hydroxy-3,3,20-trimethyl-prostanoic acid |
| 718 | 417 | 9α-hydroxy-11α-methoxy-15-hydroxy-3-oxa-prostanoic acid |
| 719 | 419 | 9α-hydroxy-11α-methoxy-15-hydroxy-3-oxa-16,16-dimethyl-prostanoic acid |
| 720 | 422 | 9α-hydroxy-11α-methoxy-15-hydroxy-2-fluoro- |

TABLE 15-continued

| Example | Starting 13-trans-prostenoic acid or ester of Example | Product 11-oxy-15-oxy-prostanoic acid or ester |
|---|---|---|
| 721 | 424 | 18,20-ethano-prostanoic acid |
|  |  | 9α-hydroxy-11α-methoxy-15-hydroxy-7,20-dinor-prostanoic acid |
| 722 | 426 | 9α-hydroxy-11α-methoxy-15-hydroxy-7a-homo-20-methyl-prostanoic acid |
| 723 | 429 | 9α-hydroxy-11α-methoxy-15-hydroxy-2-phenyl-17,17-dimethyl-prostanoic acid |
| 724 | 431 | 9α-hydroxy-11α-ethoxy-15-hydroxy-16,16-dimethyl-prostanoic acid |
| 725 | 432 | 9α-hydroxy-11α-ethoxy-15-hydroxy-16-methyl-18,20-ethano-prostanoic acid |
| 726 | 435 | 9α-hydroxy-11α-propoxy-15-hydroxy-16,16-dimethyl-prostanoic acid |
| 727 | 437 | 9α-hydroxy-11α-propoxy-15-hydroxy-prostanoic acid |
| 728 | 441 | 9α-hydroxy-11α-propoxy-15-methoxy-prostanoic acid |
| 729 | 442 | 9α-hydroxy-11α-propoxy-15-hydroxy-16,16-dimethyl-prostanoic acid |
| 730 | 443 | 9α-hydroxy-11α-isopropoxy-15-hydroxy-20-nor-16,19-methano-prostanoic acid |
| 731 | 444 | 9α-hydroxy-11α-isopropoxy-15-hydroxy-prostanoic acid |
| 732 | 445 | 9α-hydroxy-4-n-butoxy-15-hydroxy-16,16-dimethyl-prostanoic acid |
| 733 | 446 | 9α-hydroxy-4-n-butoxy-15-hydroxy-protanoic acid |
| 734 | 451 | 9α-hydroxy-11α-methoxy-15-hydroxy-2,16,16-trimethyl-prostanoic acid |
| 735 | 452 | 9α-hydroxy-11α-methoxy-15-hydroxy-2-methyl-prostanoic acid |
| 736 | 453 | ethyl 9α-hydroxy-11α-ethoxy-15-hydroxy-prostanoate |
| 737 | 454 | ethyl 9α-hydroxy-11α-ethoxy-15-hydroxy-20-methyl-17,20-ethano-prostanoate |
| 738 | 455 | methyl 9α-hydroxy-11α-methoxy-15-hydroxy-16,16-methyl-prostanoate |
| 739 | 461 | ethyl 9α-hydroxy-11α-butoxy-15-methoxy-2-ethyl-prostanoate |
| 740 | 462 | ethyl 9α-hydroxy-11α-butoxy-15-hydroxy-2-ethyl-16,16-dimethyl-prostanoate |
| 741 | 463 | ethyl 9α-hydroxy-11α-methoxy-15-hydroxy-3,3-dimethyl-prostanoate |
| 742 | 464 | ethyl 9α-hydroxy-11α-methoxy-15-hydroxy-3,3,16,16-tetramethyl-prostanoate |
| 743 | 465 | ethyl 9α-hydroxy-11α-ethoxy-15-hydroxy-3-oxa-20-ethyl-prostanoate |
| 744 | 467 | ethyl 9α-hydroxy-11α-sec-butoxy-15-hydroxy-7-nor-20-methyl-prostanoate |
| 745 | 469 | ethyl 9α-hydroxy-11α-methoxy-15-hydroxy-7α-homo-17,20-(1,3-propano)-prostanoate |
| 746 | 472 | butyl 9α-hydroxy-11α-methoxy-15-hydroxy-16,16-dimethyl-prostanoate |
| 747 | 473 | butyl 9α-hydroxy-11α-methoxy-15-hydroxy-prostanoate |
| 748 | 474 | isopropyl 9α-hydroxy-11α-methoxy-15-hydroxy-16,16-dimethyl-prostanoate |
| 749 | 475 | isopropyl 9α-hydroxy-11α-methoxy-15-hydroxy-prostanoate |
| 750 | 477 | isopropyl 9α-hydroxy-11α-methoxy-15-hydroxy-17,18-cis-methano-prostanoate |
| 751 | 478 | decyl 9α-hydroxy-11α-methoxy-15-hydroxy-prostanoate |
| 752 | 479 | decyl 9α-hydroxy-11α-methoxy-15-hydroxy-16,16-dimethyl-prostanoate |
| 753 | 480 | decyl 9α-hydroxy-11α-methoxy-15-hydroxy-20-ethyl-prostanoate |
| 754 | 481 | decyl 9α-hydroxy-11α-methoxy-15-hydroxy-17,20-(1,3-propano)-prostanoate |
| 755 | 483 | ethyl 9α-hydroxy-11α-t-butoxy-15-hydroxy-prostanoate |
| 756 | 484 | ethyl 9α-hydroxy-11α-t-butoxy-15-hydroxy-16,16-dimethyl-prostanoate |
| 757 | 486 | 9α-hydroxy-11α-(2-hydroxyethoxy)-15-hydroxy-prostanoic acid |
| 758 | 487 | 9α-hydroxy-11α-(2-hydroxyethoxy)-15-hydroxy-16,16-dimethyl-prostanoic acid |
| 759 | 488 | 9α-hydroxy-11α-(2-hydroxyethoxy)-15-hydroxy-17,18-cis-methano-prostanoic acid |
| 760 | 489 | 9α-hydroxy-11α-(2-hydroxyethoxy)-15-hydroxy-16,17,18,19,20-pentanor-15-(1-adamantyl)-prostanoic acid |
| 761 | 490 | 9α-hydroxy-11α-(2-hydroxyethoxy)-15-hydroxy-20-ethyl-prostanoic acid |
| 762 | 491 | 9α-hydroxy-11α-(2-hydroxyethoxy)-15-hydroxy-16-ethyl-prostanoic acid |
| 763 | 492 | 9α-hydroxy-11α-(2-hydroxyethoxy)-15-hydroxy-16,20-ethano-prostanoic acid |
| 764 | 493 | 9α-hydroxy-11α-(2-hydroxyethoxy)-15-methoxy- |

TABLE 15-continued

| Example | Starting 13-trans-prostenoic acid or ester of Example | Product 11-oxy-15-oxy-prostanoic acid or ester |
|---|---|---|
| 765 | 495 | 9α-hydroxy-11α-(2-hydroxyethoxy)-15-hydroxy-6,7,19,20-tetranor-prostanoic acid |
| 766 | 497 | 9α-hydroxy-11α-(2-hydroxyethoxy)-15-hydroxy-5,6,7,18,19,20-hexanor-prostanoic acid |
| 767 | 499 | 9α-hydroxy-11α-(2-hydroxyethoxy)-15-hydroxy-7a,7b-bishomo-20-ethyl-prostanoic acid |
| 768 | 500 | 9α-hydroxy-11α-(2-hydroxyethoxy)-15-hydroxy-7a,7b-bishomo-16,16-dimethyl-prostanoic acid |
| 769 | 502 | 9α-hydroxy-11α-(2-hydroxyethoxy)-15-hydroxy-7a,7b-bishomo-16,20-(1,3-propano)-prostanoic acid |
| 770 | 505 | 9α-hydroxy-11α-(2-hydroxyethoxy)-15-hydroxy-3,3-dimethyl-prostanoic acid |
| 771 | 508 | 9α-hydroxy-11α-(2-hydroxyethoxy)-15-hydroxy-3-oxa-prostanoic acid |
| 772 | 509 | 9α-hydroxy-11α-(2-hydroxyethoxy)-15-hydroxy-3-oxa-16,16-dimethyl-prostanoic acid |
| 773 | 510 | 9α-hydroxy-11α-(2-hydroxyethoxy)-15-hydroxy-3-oxa-16,19-trans-ethano-prostanoic acid |
| 774 | 511 | 9α-hydroxy-11α-(2-hydroxyethoxy)-15-methoxy-3-oxa-prostanoic acid |
| 775 | 514 | 9α-hydroxy-11α-(2-hydroxyethoxy)-15-hydroxy-2-fluoro-16,16-dimethyl-prostanoic acid |
| 776 | 515 | 9α-hydroxy-11α-(2-hydroxyethoxy)-15-hydroxy-2-fluoro-prostanoic acid |
| 777 | 517 | 9α-hydroxy-11α-(2-hydroxyethoxy)-15-hydroxy-7,20-bisnor-prostanoic acid |
| 778 | 519 | 9α-hydroxy-11α-(2-hydroxyethoxy)-15-hydroxy-7α-homo-20-methyl-prostanoic acid |
| 779 | 520 | 9α-hydroxy-11α-(2-hydroxyethoxy)-15-hydroxy-7a-homo-16,-dimethyl-prostanoic acid |
| 780 | 522 | 9α-hydroxy-11α-(2-hydroxyethoxy)-15-hydroxy-2-phenyl-prostanoic acid |
| 781 | 523 | 9α-hydroxy-11α-(2-hydroxypropoxy)-15-hydroxy-prostanoic acid |
| 782 | 524 | 9α-hydroxy-11α-(2-hydroxypropoxy)-15-hydroxy-16,16-dimethyl-prostanoic acid |
| 783 | 527 | 9α-hydroxy-11α-(4-hydroxybutoxy)-15-hydroxy-prostanoic acid |
| 784 | 528 | 9α-hydroxy-11α-(4-hydroxybutoxy)-15-hydroxy-16,16-dimethyl-prostanoic acid |
| 785 | 529 | ethyl 9α-hydroxy-11α-(2-hydroxyethoxy)-15-hydroxy-16,16-dimethyl-prostanoate |
| 786 | 531 | ethyl 9α-hydroxy-11α-(2-hydroxyethoxy)-15-hydroxy-19,20-dinor-16,17-(1,3-propano)-prostanoate |
| 787 | 533 | methyl-9α-hydroxy-11α-(2-hydroxyethoxy)-15-hydroxy-20-nor-prostanoate |
| 788 | 534 | methyl-9α-hydroxy-11α-(2-hydroxyethoxy)-15-methoxy-prostanoate |
| 789 | 537 | ethyl 9α-hydroxy-11α-(2-hydroxyethoxy)-15-hydroxy-7a,7b-bishomo-17,18-cis-methano-prostanoate |
| 790 | 544 | ethyl 9α-hydroxy-11α-(3-hydroxypropoxy)-15-hydroxy-3-oxa-16,16-dimethyl-prostanoate |
| 791 | 545 | ethyl 9α-hydroxy-11α-(3-hydroxypropoxy)-15-hydroxy-3-oxa-16,20-methano-prostanoate |
| 792 | 546 | butyl 9α-hydroxy-11α-(2-hydroxyethoxy)-15-hydroxy-prostenoate |
| 793 | 547 | butyl 9α-hydroxy-11α-(2-hydroxyethoxy)-15-hydroxy-16,16-dimethyl-prostanoate |
| 794 | 548 | butyl 9α-hydroxy-11α-(2-hydroxyethoxy)-15-hydroxy-17,18-cis-methano-prostanoate |
| 795 | 549 | butyl 9α-hydroxy-11α-(2-hydroxyethoxy)-15-hydroxy-17,19-(1,3-propano)-prostanoate |
| 796 | 554 | isopropyl 9α-hydroxy-11α-(2-hydroxyethoxy)-15-hydroxy-16,16-dimethyl-prostanoate |
| 797 | 556 | decyl 9α-hydroxy-11α-(2-hydroxyethoxy)-15-hydroxy-prostanoate |
| 798 | 557 | decyl 9α-hydroxy-11α-(2-hydroxyethoxy)-15-hydroxy-16,16-dimethyl-prostanoate |
| 799 | 558 | decyl 9α-hydroxy-11α-(2-hydroxyethoxy)-15-methoxy-prostanoate |
| 800 | 559 | decyl 9α-hydroxy-11α-(2-hydroxyethoxy)-15-hydroxy-20-nor-17,18-trans-(1,3-propano)-prostanoate |
| 801 | 562 | 9-oxo-11α-methoxy-15-hydroxy-15-methyl-20-ethyl-prostanoic acid |
| 802 | 564 | 9-oxo-11α-methoxy-15-hydroxy-15-methyl-6,7,19,20-tetranor-prostanoic acid |
| 803 | 565 | 9-oxo-11α-ethoxy-15-hydroxy-15-methyl-5,6,7,18,19,20-hexanor-prostanoic acid |
| 804 | 566 | 9-oxo-11α-methyl-15-hydroxy-15-methyl-7a,7b-bishomo-20-ethyl- |

TABLE 15-continued

| Example | Starting 13-trans-prostenoic acid or ester of Example | Product 11-oxy-15-oxy-prostanoic acid or ester |
|---|---|---|
| 805 | 567 | 9-oxo-11α-methoxy-15-hydroxy-15-methyl-2-ethyl-20-nor-prostanoic acid |
| 806 | 568 | 9-oxo-11α-methoxy-15-hydroxy-15-methyl-3,3,20-trimethyl-prostanoic acid |
| 807 | 569 | 9-oxo-11α-methoxy-15-hydroxy-15-methyl-3-oxa-prostanoic acid |
| 808 | 571 | 9-oxo-11α-methoxy-15-hydroxy-15-methyl-2-fluoro-18,20-ethano-prostanoic acid |
| 809 | 572 | 9-oxo-11α-methoxy-15-hydroxy-15-methyl-7,20-dinor-prostanoic acid |
| 810 | 573 | 9-oxo-11α-methoxy-15-hydroxy-15-methyl-7-nor-17,20-(1,4-butano)-prostanoic acid |
| 811 | 574 | 9-oxo-11α-methoxy-15-hydroxy-15-methyl-7a-homo-20-methyl-prostanoic acid |
| 812 | 575 | 9-oxo-11α-methoxy-15-hydroxy-15-methyl-7a-homo-17,18-cis-methano-prostanoic acid |
| 813 | 576 | 9-oxo-11α-methoxy-15-hydroxy-15-methyl-7a-homo-20-cyclopentyl-prostanoic acid |
| 814 | 577 | 9-oxo-11α-methoxy-15-hydroxy-15-methyl-2-phenyl-18,20-(1,3-propano)-prostanoic acid |
| 815 | 580 | 9-oxo-11α-propoxy-15-hydroxy-15-methyl-20-nor-prostanoic acid |
| 816 | 581 | 9-oxo-11α-propoxy-15-hydroxy-15-methyl-prostanoic acid |
| 817 | 583 | 9-oxo-11α-isopropoxy-15-hydroxy-15-methyl-prostanoic acid |
| 818 | 584 | 9-oxo-4-n-butoxy-15-hydroxy-15-methyl-prostanoic acid |
| 819 | 585 | 9-oxo-11α-methoxy-15-hydroxy-15-methyl-2-methyl-prostanoic acid |
| 820 | 586 | 9-oxo-11α-(2-hydroxy-ethoxy)-15-hydroxy-15-methyl-prostanoic acid |
| 821 | 587 | 9-oxo-11α-(2-hydroxy-ethoxy)-15-hydroxy-15-methyl-17,18-cis-methano-prostanoic acid |
| 822 | 588 | 9-oxo-11α-(2-hydroxy-ethoxy-15-hydroxy-15-methyl-20-ethyl-prostanoic acid |
| 823 | 590 | 9-oxo-11α-(2-hydroxy-ethoxy)-15-hydroxy-15-methyl-6,7,19,20-tetranor-prostanoic acid |
| 824 | 591 | 9-oxo-11α-(2-hydroxy-ethoxy)-15-hydroxy-15-methyl-5,6,7,18,19,20-hexanor-prostanoic acid |
| 825 | 592 | 9-oxo-11α-(2-hydroxy-ethoxy)-15-hydroxy-15-methyl-7a,7b-bis-homo-20-ethyl-prostanoic acid |
| 826 | 593 | 9-oxo-11α-(β-hydroxy-ethoxy)-15-hydroxy-15-methyl-7a,7b-bis-homo-prostanoic acid |
| 827 | 594 | 9-oxo-11α-(2-hydroxy-ethoxy)-15-hydroxy-15-methyl-2-ethyl-20-cyclopentyl-prostanoic acid |
| 828 | 596 | 9-oxo-11α-(2-hydroxy-ethoxy)-15-hydroxy-15-methyl-3,3-dimethyl-prostanoic acid |
| 829 | 597 | 9-oxo-11α-(2-hydroxy-ethoxy)-15-hydroxy-15-methyl-3-oxa-prostanoic acid |
| 830 | 599 | 9-oxo-11α-(2-hydroxy-ethoxy)-15-hydroxy-15-methyl-2-fluoro-prostanoic acid |
| 831 | 600 | 9-oxo-11α-(2-hydroxy-ethoxy)-15-hydroxy-15-methyl-7,20-bisnor-prostanoic acid |
| 832 | 601 | 9-oxo-11α-(2-hydroxy-ethoxy)-15-hydroxy-15-methyl-7a-homo-20-methyl-prostanoic acid |
| 833 | 602 | 9-oxo-11α-(2-hydroxy-ethoxy)-15-hydroxy-15-methyl-2-phenyl-prostanoic acid |
| 834 | 603 | 9-oxo-11α-(2-hydroxy-propoxy-15-hydroxy-15-methyl-prostanoic acid |
| 835 | 605 | 9-oxo-11α-(4-hydroxy-butoxy)-15-hydroxy-15-methyl-prostanoic acid |

EXAMPLE 836

Preparation of 9α/β,15-dihydroxy-11α-methoxy-13-trans-prostenoic acid

A solution containing 200 mg. of 9-oxo-11α-methoxy-15-hydroxy-13-trans-prostenoic acid (Example 227) and 20 mg. of sodium borohydride in 1 ml. of absolute alcohol is stirred at ambient temperature for 18 hours. The solution is diluted with 30 ml. of water, acidified with 2N hydrochloric acid and extracted with ether several times. The combined extracts are washed with saturated sodium chloride, dried with anhydrous magnesium sulfate and taken to dryness to give an oily product, which is a mixture of 9α- and 9β-hydroxy derivatives, separable by chromatography.

EXAMPLE 837

Preparation of 4,4-dimethyl-3-triphenylmethoxy-1-octyne

Treatment of 23.1 g. (0.150 mole) of 4,4-dimethyl-1-octyn-3-ol (Example 149) with 56.5 g. of triphenylmethyl bromide in 150 ml. of pyridine and purification of Florisil ®, all as described in Example 127 gives the title compound, m.p. 75°–77° C.

EXAMPLE 838

Preparation of 4,4-dimethyl-1-iodo-3-triphenylmethoxy-trans-1-octene

To 256 ml. of a 0.42 N solution of disiamylborane in diglyme cooled to 0° C. under an inert atmosphere is added 39.6 g. (0.10 mole) of 4,4-dimethyl-3-triphenylmethoxy-1-octyne (Example 837). The cooling bath is removed and the mixture is stirred at ambient temperature for 3 hours. The mixture is cooled to 0° C. and 26.3 g. (0.35 mole) of finely divided trimethylamine oxide is added over a 10 minute period, the cooling bath is removed, and the mixture is allowed to exotherm but not above 40° C. after the mixture has cooled to room temperature, it is poured into 800 ml. of 15% sodium hydroxide solution and a solution of 38.1 g. of iodine in 100 ml. of tetrahydrofuran is added immediately. The mixture is stirred at room temperature for 0.5 hour and is partitioned between water and ether. The organic phase is decolorized with 5% sodium thiosulfate solution and is washed with water and saturated brine, dried (NaSO₄) and evaporated. The residue is purified by passing through a column of Florisil and eluting with 5–15% (v/v) benzene in hexane to yield the title compound.

We claim:

1. A racemic compound of the formula:

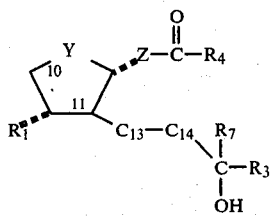

wherein $R_1$ is W-hydroxy-subsituted $C_2$–$C_4$ alkoxy; $R_3$ is a straight chain alkyl group having from 2 to 10 carbon atoms, a straight chain alkyl group having from 2 to 10 carbon atoms and substituted with one or two lower alkyl groups, a straight chain alkenyl methyl group having from 3 to 10 atoms, a straight chain alkenyl methyl group having from 3 to 10 carbon atoms and substituted with one or two lower alkyl groups, a cycloalkyl group having from 4 to 9 atoms, lower alkyl substituted cycloalkyl group having from 5 to 10 carbon atoms, a cycloalkyl-substituted lower alkyl group having from 6 to 12 carbon atoms and in which the cycoalkyl group is optionally substituted with a lower alkyl group, a cycloalkenyl group having from 5 to 9 carbon atoms, a lower alkyl substituted cycloalkenyl group having 6 to 10 carbon atoms, a cycloalkenyl substituted lower alkyl group having from 6 to 12 carbon atoms and in which the cycoalkenyl group is optionally substituted with a lower alkyl group; $R_4$ is hydroxy or an alkoxy group having from 1 to 12 carbon atoms; $R_7$ is hydrogen or a lower alkyl group having up to 3 carbon atoms; Y is

Z is

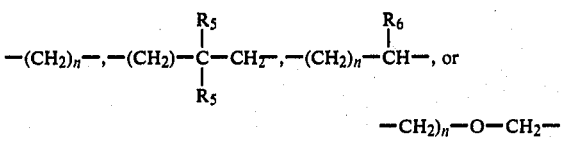

wherein n is an integer from 3 to 8, inclusive, $R_5$ is an alkyl group having up to 3 carbon atoms, and $R_6$ is an alkyl group having up to 3 carbon atoms, a flourine atom or a phenyl group; and the moiety $-C_{13}-C_{14}-$ is trans-vinylene.

2. A racemic compound according to claim 1, wherein $R_1$, $R_3$, $R_4$, $R_7$, and $C_{13}$–$C_{14}$ are as previously defined; and Z is the divalent radical $-(CH_2)_n-$, wherein n is as previously defined.

3. A compound of claim 1, 9-oxo-11α-(2-hydroxyethoxy)-15-hydroxy-13-trans-prostenoic acid.

4. A compound of claim 1, 9-oxo-11α-(2-hydroxyethoxy)-15-hydroxy-15-methyl-13-trans-prostenoic acid.

5. A compound of claim 1, 9-oxo-11α-(2-hydroxyethoxy)-15-hydroxy-16,16-dimethyl-13-trans-prostenoic acid.

6. A compound of claim 1, 9-oxo-11α-(2-hydroxyethoxy)-15-hydroxy-13-trans,17-cis-prostadienoic acid.

7. A compound of claim 1, 9-oxo-11α-(2-hydroxyethoxy)-15-hydroxy-15-methyl-13-trans,17-cis-prostadienoic acid.

8. A compound of claim 1, 9-oxo-11α-(2-hydroxyethoxy)-15-hydroxy-15-methyl-17,18-cis-methano-13-trans-prostenoic acid.

9. A compound of claim 1, 9α,15-dihydroxy-11α-(2-hydroxyethoxy)-13-trans-prostenoic acid.

10. A compound of claim 1, 9α,15-dihydroxy-11α-(2-hydroxyethoxy)-13-trans-prostenoic acid.

11. A compound of claim 1, 9α,15-dihydroxy-11α-(2-hydroxyethoxy)-16,16-dimethyl-13-trans-prostenoic acid.

12. A compound of claim 1, 9α,15-dihydroxy-11α-(2-hydroxyethoxy)-13-trans,17-cis-prostadienoic acid.

13. A compound of claim 1, 9α,15-dihydroxy-11α-(2-hydroxyethoxy)-15-methyl-13-trans,17-cis-prostadienoic acid.

14. A compound of claim 1, 9α,15-dihydroxy-11α-(2-hydroxyethoxy)-15-methyl-17,18-cis-methano-13-trans-prostenoic acid.

* * * * *